(12) United States Patent
Podbielski

(10) Patent No.: US 7,169,902 B2
(45) Date of Patent: Jan. 30, 2007

(54) **COLLAGEN-BINDING PROTEINS FROM *STREPTOCOCCUS PYOGENES***

(76) Inventor: Andreas Podbielski, Dept. of Medical Microbiology & Hygiene, University Hospital, Robert-Koch-Str. 8, D-89081 Ulm (DE)

( * ) Notice: Subject to any disclaimer, the term of this patent is extended or adjusted under 35 U.S.C. 154(b) by 324 days.

(21) Appl. No.: 10/854,191

(22) Filed: May 27, 2004

(65) Prior Publication Data

US 2005/0019345 A1    Jan. 27, 2005

Related U.S. Application Data

(62) Division of application No. 09/494,297, filed on Jan. 31, 2000, now Pat. No. 6,777,547.

(51) Int. Cl.
*C07K 16/00* (2006.01)
*A61K 39/395* (2006.01)
*G01N 33/53* (2006.01)

(52) U.S. Cl. .............................. 530/387.1; 424/130.1; 435/7.1

(58) Field of Classification Search .................. None
See application file for complete search history.

(56) References Cited

OTHER PUBLICATIONS

Podbielski et al, Molecular Microbiology 31 (4), 1051 (1999).*

* cited by examiner

*Primary Examiner*—James Martinell
(74) *Attorney, Agent, or Firm*—B. Aaron Schulman; Stites & Harbison PLLC

(57) ABSTRACT

Isolated proteins, designated Cpa1 and Cpa49, and their corresponding amino acid and nucleic acid sequences are provided which are useful in the prevention and treatment of infection caused by group A streptococcal bacteria such as *Streptococcus pyogenes*. These proteins have been observed to bind to collagen, and thus methods are provided, such as by administration of the proteins or antibodies generated thereto, whereby streptococcal binding of collagen can be inhibited, and streptococcal infection can be greatly reduced. In addition, medical instruments can be treated using the collagen-binding proteins of the invention in order to reduce or eliminate the possibility of their becoming infected or further spreading the infection. In particular, the proteins are advantageous because they may be used as vaccine components or antibodies thereof, and they may be administered to wounds or used to coat biomaterials in order to act as collagen blocking agents and reduce or prevent severe infection by group A streptococcal bacteria.

5 Claims, 5 Drawing Sheets

Figure 1:
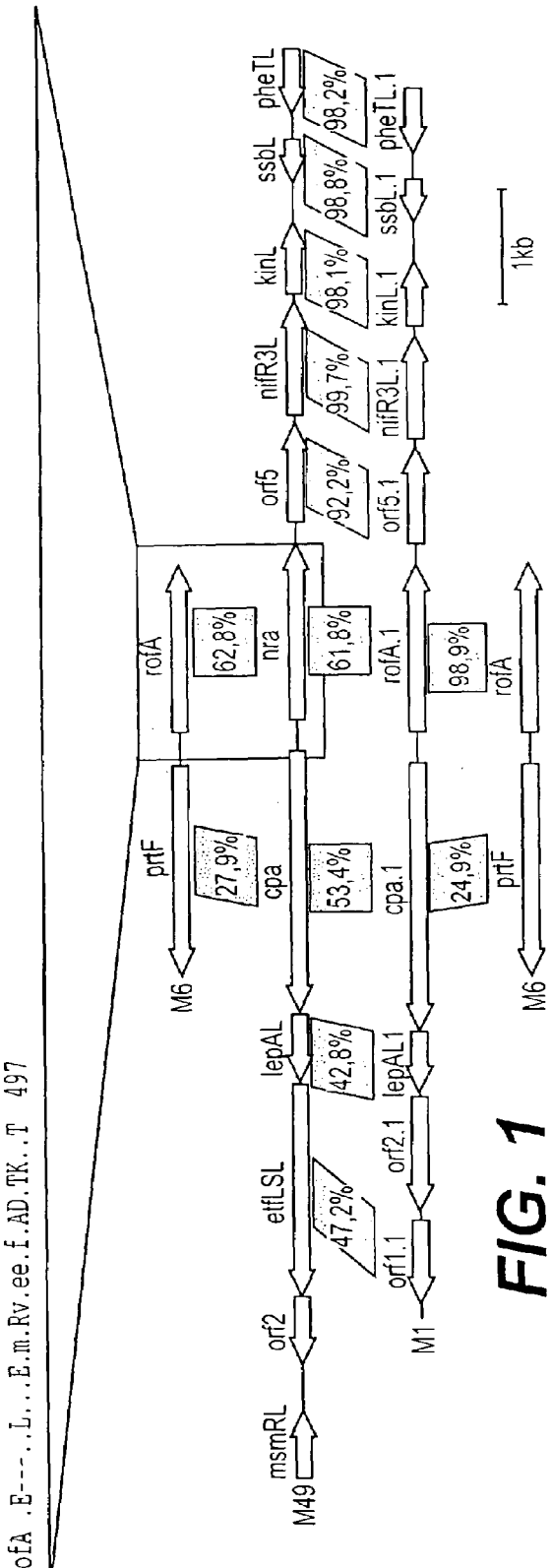

TRANSCRIPT ANALYSIS OF SELECTED GENES
IN GAS wt AND nra MUTANT STRAINS

Binding to immobilized human matrix proteins by GAS wt and nra-mutant strains grown in/on THY-medium to logarithmic/stationary growth phase in an aerobic/anaerobic atmosphere

SEQUENCE LISTING

<160> NUMBER OF SEQ ID NOS: 32

<210> SEQ ID NO 1
<211> LENGTH: 2274
<212> TYPE: DNA
<213> ORGANISM: Streptococcus pyogenes

<400> SEQUENCE: 1

```
atgaaaaaaa caaggtttcc aaataagctt aatactctta atactcaaag ggtattaagt      60
aaaaactcaa aacgatttac tgtcacttta gtgggagtct ttttaatgat cttcgctttg     120
gtaacttcca tggttggtgc taagactgtt tttggtttag tagaatcctc gacgccaaac     180
gcaataaatc cagattcaag ttcggaatac agatggtatg gatatgaatc ttatgtaaga     240
gggcatccat attataaaca gtttagagta gcacacgatt taagggttaa cttagaagga     300
agtagaagtt atcaagtttt attgctttaat ttaaagaaag catttcctct cggatcagat     360
agtagtgtta aaaagtggta taaaaaacat gatggaatct ctacaaaatt tgaagattat     420
gcgatgagcc ctagaattac gggagatgag ctaaatcaga agttacgagc tgttatgtat     480
aatggacatc cacaaaatgc caatggtatt atggaaggct tggaacccttg aatgctatc     540
agagttacac aagaggcggt atggtactat tctgataatg ctcctatttc taatccagat     600
gaaagtttta aagggagtc agaaagtaac ttggttagta cttctcaatt atctttgatg     660
cgtcaagctt tgaagcaact gattgatccg aatttggcaa ctaaaatgcc aaaacaagtt     720
ccggatgatt ttcagctaag tattttttgag tctgaggaca agggagataa atataataaa     780
ggataccaaa atcttttgag tggtggttta gttcctacta aaccaccaac tccaggagac     840
ccaccaatgc ctccaaatca acctcaaacg acttcagtac ttattagaaa gtatgctata     900
ggtgattact ctaaattgct tgaaggtgca acattacagt tgacagggga taacgtgaat     960
agttttcaag cgagagtgtt tagcagtaat gatattggag aaagaattga actatcagat    1020
ggaacttata ctttaactga attgaattct ccagctggtt atagtatcgc agagccaatc    1080
acttttaagg ttgaagctgg caaagtgtat actattattg atggaaaaca gattgaaaat    1140
cccaataaag agatagtaga gccttactca gtagaagcat ataatgattt tgaagaattt    1200
agcgttttaa ctacacaaaa ctatgcaaaa ttttattatg caaaaaataa aaatggaagt    1260
tcacaggttg tctattgctt taatgcagat ctaaaatctc caccagactc tgaagatggt    1320
gggaaaacaa tgactccaga ctttacaaca ggagaagtaa aatacactca tattgcaggt    1380
cgtgacctct ttaaatatac tgtgaaacca agagataccg atcctgacac tttcttaaaa    1440
catatcaaaa aagtaattga aagggttac agggaaaaag acaagctat tgagtatagt    1500
ggtctaactg agacacaatt gcgtgcggct actcagttag caatatatta tttcactgat    1560
agtgctgaat tagataagga taaactaaaa gactatcatg gttttggaga catgaatgat    1620
agtactttag cagttgctaa aatccttgta gaatacgctc aagatagtaa tcctccacag    1680
ctaactgacc ttgatttctt tattccgaat aacaataaat atcaatctct tattggaact    1740
cagtggcatc cagaagattt agttgatatt attcgtatgg aagataaaaa agaagttata    1800
cctgtaactc ataatttaac attgagaaaa acggtgactg gtttagctgg tgacagaact    1860
aaagatttcc attttgaaat tgaattaaaa aataataagc aagaattgct ttctcaaact    1920
gttaaaacag ataaaacaaa cctcgaattt aaagatggta agcaaccat taatttaaaa    1980
catggggaaa gtttaacact tcaaggttta ccagaaggtt attcttacct tgtcaaagaa    2040
acagattctg aaggctataa ggttaaagtt aatagccaag aagtagcaaa tgctacagtt    2100
tcaaaaacag aataacaag tgatgagaca cttgcttttg aaaataataa agagcctgtt    2160
gttcctacag gagttgatca aaagatcaat ggctatctag ctttgatagt tatcgctggt    2220
atcagtttgg ggatctgggg aattcacacg ataaggataa gaaaacatga ctag          2274
```

<210> SEQ ID NO 2

```
<211> LENGTH: 757
<212> TYPE: PRT
<213> ORGANISM: Streptococcus pyogenes

<400> SEQUENCE: 2
```

| | | | | | | | | | | | | | | |
|---|---|---|---|---|---|---|---|---|---|---|---|---|---|---|
| Met | Lys | Lys | Thr | Arg | Phe | Pro | Asn | Lys | Leu | Asn | Thr | Leu | Asn | Thr | Gln |
| 1 | | | | 5 | | | | | 10 | | | | | 15 | |
| Arg | Val | Leu | Ser | Lys | Asn | Ser | Lys | Arg | Phe | Thr | Val | Thr | Leu | Val | Gly |
| | | | 20 | | | | | 25 | | | | | 30 | | |
| Val | Phe | Leu | Met | Ile | Phe | Ala | Leu | Val | Thr | Ser | Met | Val | Gly | Ala | Lys |
| | | 35 | | | | | 40 | | | | | 45 | | | |
| Thr | Val | Phe | Gly | Leu | Val | Glu | Ser | Ser | Thr | Pro | Asn | Ala | Ile | Asn | Pro |
| | 50 | | | | | 55 | | | | | 60 | | | | |
| Asp | Ser | Ser | Glu | Tyr | Arg | Trp | Tyr | Gly | Tyr | Glu | Ser | Tyr | Val | Arg |
| 65 | | | | | 70 | | | | | 75 | | | | | 80 |
| Gly | His | Pro | Tyr | Tyr | Lys | Gln | Phe | Arg | Val | Ala | His | Asp | Leu | Arg | Val |
| | | | | 85 | | | | | 90 | | | | | 95 | |
| Asn | Leu | Glu | Gly | Ser | Arg | Ser | Tyr | Gln | Val | Tyr | Cys | Phe | Asn | Leu | Lys |
| | | | | 100 | | | | | 105 | | | | | 110 | |
| Lys | Ala | Phe | Pro | Leu | Gly | Ser | Asp | Ser | Val | Lys | Lys | Trp | Tyr | Lys |
| | | | 115 | | | | | 120 | | | | | 125 | | |
| Lys | His | Asp | Gly | Ile | Ser | Thr | Lys | Phe | Glu | Asp | Tyr | Ala | Met | Ser | Pro |
| | 130 | | | | | 135 | | | | | 140 | | | | |
| Arg | Ile | Thr | Gly | Asp | Glu | Leu | Asn | Gln | Lys | Leu | Arg | Ala | Val | Met | Tyr |
| 145 | | | | | 150 | | | | | 155 | | | | | 160 |
| Asn | Gly | His | Pro | Gln | Asn | Ala | Asn | Gly | Ile | Met | Glu | Gly | Leu | Glu | Pro |
| | | | | 165 | | | | | 170 | | | | | 175 | |
| Leu | Asn | Ala | Ile | Arg | Val | Thr | Gln | Glu | Ala | Val | Trp | Tyr | Tyr | Ser | Asp |
| | | | 180 | | | | | 185 | | | | | 190 | | |
| Asn | Ala | Pro | Ile | Ser | Asn | Pro | Asp | Glu | Ser | Phe | Lys | Arg | Glu | Ser | Glu |
| | | 195 | | | | | 200 | | | | | 205 | | | |
| Ser | Asn | Leu | Val | Ser | Thr | Ser | Gln | Leu | Ser | Leu | Met | Arg | Gln | Ala | Leu |
| | 210 | | | | | 215 | | | | | 220 | | | | |
| Lys | Gln | Leu | Ile | Asp | Pro | Asn | Leu | Ala | Thr | Lys | Met | Pro | Lys | Gln | Val |
| 225 | | | | | 230 | | | | | 235 | | | | | 240 |
| Pro | Asp | Asp | Phe | Gln | Leu | Ser | Ile | Phe | Glu | Ser | Glu | Asp | Lys | Gly | Asp |
| | | | | 245 | | | | | 250 | | | | | 255 | |
| Lys | Tyr | Asn | Lys | Gly | Tyr | Gln | Asn | Leu | Leu | Ser | Gly | Leu | Val | Pro |
| | | | 260 | | | | | 265 | | | | | 270 | | |
| Thr | Lys | Pro | Pro | Thr | Pro | Gly | Asp | Pro | Met | Pro | Pro | Asn | Gln | Pro |
| | 275 | | | | | 280 | | | | | 285 | | | | |
| Gln | Thr | Thr | Ser | Val | Leu | Ile | Arg | Lys | Tyr | Ala | Ile | Gly | Asp | Tyr | Ser |
| | 290 | | | | | 295 | | | | | 300 | | | | |
| Lys | Leu | Leu | Glu | Gly | Ala | Thr | Leu | Gln | Leu | Thr | Gly | Asp | Asn | Val | Asn |
| 305 | | | | | 310 | | | | | 315 | | | | | 320 |
| Ser | Phe | Gln | Ala | Arg | Val | Phe | Ser | Ser | Asn | Asp | Ile | Gly | Glu | Arg | Ile |
| | | | | 325 | | | | | 330 | | | | | 335 | |
| Glu | Leu | Ser | Asp | Gly | Thr | Tyr | Thr | Leu | Thr | Glu | Leu | Asn | Ser | Pro | Ala |
| | | | 340 | | | | | 345 | | | | | 350 | | |
| Gly | Tyr | Ser | Ile | Ala | Glu | Pro | Ile | Thr | Phe | Lys | Val | Glu | Ala | Gly | Lys |
| | | 355 | | | | | 360 | | | | | 365 | | | |
| Val | Tyr | Thr | Ile | Ile | Asp | Gly | Lys | Gln | Ile | Glu | Asn | Pro | Asn | Lys | Glu |
| 370 | | | | | 375 | | | | | 380 | | | | | |
| Ile | Val | Glu | Pro | Tyr | Ser | Val | Glu | Ala | Tyr | Asn | Asp | Phe | Glu | Glu | Phe |

```
             385                 390                 395                 400
Ser Val Leu Thr Thr Gln Asn Tyr Ala Lys Phe Tyr Tyr Ala Lys Asn
                405                 410                 415
Lys Asn Gly Ser Ser Gln Val Val Tyr Cys Phe Asn Ala Asp Leu Lys
                420                 425                 430
Ser Pro Pro Asp Ser Glu Asp Gly Gly Lys Thr Met Thr Pro Asp Phe
                435                 440                 445
Thr Thr Gly Glu Val Lys Tyr Thr His Ile Ala Gly Arg Asp Leu Phe
                450                 455                 460
Lys Tyr Thr Val Lys Pro Arg Asp Thr Asp Pro Asp Thr Phe Leu Lys
465                 470                 475                 480
His Ile Lys Lys Val Ile Glu Lys Gly Tyr Arg Glu Lys Gly Gln Ala
                485                 490                 495
Ile Glu Tyr Ser Gly Leu Thr Glu Thr Gln Leu Arg Ala Ala Thr Gln
                500                 505                 510
Leu Ala Ile Tyr Tyr Phe Thr Asp Ser Ala Glu Leu Asp Lys Asp Lys
                515                 520                 525
Leu Lys Asp Tyr His Gly Phe Gly Asp Met Asn Asp Ser Thr Leu Ala
                530                 535                 540
Val Ala Lys Ile Leu Val Glu Tyr Ala Gln Asp Ser Asn Pro Pro Gln
545                 550                 555                 560
Leu Thr Asp Leu Asp Phe Phe Ile Pro Asn Asn Lys Tyr Gln Ser
                565                 570                 575
Leu Ile Gly Thr Gln Trp His Pro Glu Asp Leu Val Asp Ile Ile Arg
                580                 585                 590
Met Glu Asp Lys Lys Glu Val Ile Pro Val Thr His Asn Leu Thr Leu
                595                 600                 605
Arg Lys Thr Val Thr Gly Leu Ala Gly Asp Arg Thr Lys Asp Phe His
                610                 615                 620
Phe Glu Ile Glu Leu Lys Asn Asn Lys Gln Glu Leu Leu Ser Gln Thr
625                 630                 635                 640
Val Lys Thr Asp Lys Thr Asn Leu Glu Phe Lys Asp Gly Lys Ala Thr
                645                 650                 655
Ile Asn Leu Lys His Gly Glu Ser Leu Thr Leu Gln Gly Leu Pro Glu
                660                 665                 670
Gly Tyr Ser Tyr Leu Val Lys Glu Thr Asp Ser Glu Gly Tyr Lys Val
                675                 680                 685
Lys Val Asn Ser Gln Glu Val Ala Asn Ala Thr Val Ser Lys Thr Gly
                690                 695                 700
Ile Thr Ser Asp Glu Thr Leu Ala Phe Glu Asn Asn Lys Glu Pro Val
705                 710                 715                 720
Val Pro Thr Gly Val Asp Gln Lys Ile Asn Gly Tyr Leu Ala Leu Ile
                725                 730                 735
Val Ile Ala Gly Ile Ser Leu Gly Ile Trp Gly Ile His Thr Ile Arg
                740                 745                 750
Ile Arg Lys His Asp
        755

<210> SEQ ID NO 3
<211> LENGTH: 2229
<212> TYPE: DNA
<213> ORGANISM: Streptococcus pyogenes

<400> SEQUENCE: 3
```

```
ttgcaaaaga gggataaaac caattatgga agcgctaaca acaaacgacg acaaacgacg      60
atcggattac tgaaagtatt tttgacgttt gtagctctga taggaatagt agggttttct     120
atcagagcgt tcggagctga agaacaatca gtaccaaata gacaaagctc aattcaagat     180
tatccgtggt atggctatga ttcttatcct aaaggctacc cagactatag tccgttaaag     240
acttaccata atttaaaagt aaatttagag ggaagtaagg attatcaagc atactgcttt     300
aatttaacaa acatttttcc atccaagtca gatagtgtta gatcacaatg gtataaaaaa     360
cttgaaggaa ctaatgaaaa ctttatcaag ttagcagata aaccaagaat agaagacgga     420
cagttacaac aaaatatatt gaggattctc tataatggat atcctaataa tcgtaatggg     480
ataatgaaag ggatagatcc tctaaacgct attttagtga ctcaaaatgc tatttggtat     540
actgattcag ctcaaattaa tccggatgaa agttttaaaa cagaagctcg aagtaatggt     600
attaatgacc agcagttagg cttaatgcga aaagctttaa agaactaat tgatccaaac      660
ttagggtcaa aatattcgaa taaaactcca tcaggttatc ggttaaatgt atttgaatct     720
catgataagc ctttccaaaa tcttttgagt gctgagtatg ttccggatac tcccccaaaa     780
ccaggagaag agcctccggc taaaactgaa aaaacatcag tcattatcag aaaatatgcg     840
gaaggtgact ctaaacttct agagggagca accttaaagc tttctcaaat tgaaggaagt     900
ggttttcaag aaaaagactt tcaaagtaat agtttaggag aaactgtcga attaccaaat     960
gggacttata ccttaacaga aacatcatct ccagatggat ataaaattgc ggagccgatt    1020
aagtttagag tagagaataa aaaagtattt atcgtccaaa aagatggttc tcaagtggaa    1080
aatccaaaca aagaagtagc agagccatac tcagtggaag cgtataatga ctttatggat    1140
gaagaagtac tctcgggttt tactccatac ggaaaattct attacgctac aaataaggat    1200
aaaagttcac aagttgtcta ctgcttcaat gctgatttac actcaccacc tgactcatat    1260
gatagtggtg agactataaa tccagatact agtacgatga agaagtcaa gtacacacat     1320
acggcaggta gtgacttgtt taaatatgcg ctaagaccga gagatacaaa tccagaagac    1380
ttcttaaagc acattaaaaa agtaattgaa aaaggctaca agaaaaaagg tgatagctat    1440
aatggattaa cagaaacaca gtttcgcgcg gctactcagc ttgctatcta ttattttaca    1500
gacagtgctg acttaaaaac cttaaaaact tataacaatg ggaaaggtta ccatggatttt   1560
gaatctatgg atgaaaaaac cctagctgtc acaaaagaat taattactta tgctcaaaat    1620
ggcagtgccc ctcaactaac aaatcttgat ttcttcgtac ctaataatag caaagaccaa    1680
tctcttattg ggacagaatg ccatccagat gatttggttg acgtgattcg tatggaagat    1740
aaaaagcaag aagttattcc agtaactcac agtttgacag tgaaaaaaac agtagtcggt    1800
gagttgggag ataaaactaa aggcttccaa tttgaacttg agttgaaaga taaaactgga    1860
cagcctattg ttaacactct aaaaactaat aatcaagatt tagtagctaa agatgggaaa    1920
tattcattta atctaaagca tggtgacacc ataagaatga aaggattacc gacgggtatt    1980
tcttatactc tgaaagaggc tgaagctaag gattatatag taaccgttga taacaaagtt    2040
agtcaagaag cgcagtcagt aggtaaggat ataacgaaag acaaaaaagt cacttttgaa    2100
aaccgaaaag atcttgtccc accaactggt ttgacaacag atgggctat ctatctttgg     2160
ttgttattac ttgttccact tgggttattg gtttggctat ttggtcgtaa agggttaaaa    2220
aatgactaa                                                             2229
```

<210> SEQ ID NO 4
<211> LENGTH: 742

-continued

```
<212> TYPE: PRT
<213> ORGANISM: Streptococcus pyogenes

<400> SEQUENCE: 4
```

| | | | | | | | | | | | | | | | |
|---|---|---|---|---|---|---|---|---|---|---|---|---|---|---|---|
| Met | Gln | Lys | Arg | Asp | Lys | Thr | Asn | Tyr | Gly | Ser | Ala | Asn | Asn | Lys | Arg |
| 1 | | | | 5 | | | | | 10 | | | | | 15 | |
| Arg | Gln | Thr | Thr | Ile | Gly | Leu | Leu | Lys | Val | Phe | Leu | Thr | Phe | Val | Ala |
| | | | 20 | | | | | 25 | | | | | 30 | | |
| Leu | Ile | Gly | Ile | Val | Gly | Phe | Ser | Ile | Arg | Ala | Phe | Gly | Ala | Glu | Glu |
| | | | 35 | | | | 40 | | | | | 45 | | | |
| Gln | Ser | Val | Pro | Asn | Arg | Gln | Ser | Ser | Ile | Gln | Asp | Tyr | Pro | Trp | Tyr |
| | 50 | | | | | 55 | | | | | 60 | | | | |
| Gly | Tyr | Asp | Ser | Tyr | Pro | Lys | Gly | Tyr | Pro | Asp | Tyr | Ser | Pro | Leu | Lys |
| 65 | | | | | 70 | | | | | 75 | | | | | 80 |
| Thr | Tyr | His | Asn | Leu | Lys | Val | Asn | Leu | Glu | Gly | Ser | Lys | Asp | Tyr | Gln |
| | | | | 85 | | | | | 90 | | | | | 95 | |
| Ala | Tyr | Cys | Phe | Asn | Leu | Thr | Lys | His | Phe | Pro | Ser | Lys | Ser | Asp | Ser |
| | | | 100 | | | | | 105 | | | | | 110 | | |
| Val | Arg | Ser | Gln | Trp | Tyr | Lys | Lys | Leu | Glu | Gly | Thr | Asn | Glu | Asn | Phe |
| | | 115 | | | | | 120 | | | | | 125 | | | |
| Ile | Lys | Leu | Ala | Asp | Lys | Pro | Arg | Ile | Glu | Asp | Gly | Gln | Leu | Gln | Gln |
| | 130 | | | | | 135 | | | | | 140 | | | | |
| Asn | Ile | Leu | Arg | Ile | Leu | Tyr | Asn | Gly | Tyr | Pro | Asn | Asn | Arg | Asn | Gly |
| 145 | | | | | 150 | | | | | 155 | | | | | 160 |
| Ile | Met | Lys | Gly | Ile | Asp | Pro | Leu | Asn | Ala | Ile | Leu | Val | Thr | Gln | Asn |
| | | | | 165 | | | | | 170 | | | | | 175 | |
| Ala | Ile | Trp | Tyr | Thr | Asp | Ser | Ala | Gln | Ile | Asn | Pro | Asp | Glu | Ser | Phe |
| | | | 180 | | | | | 185 | | | | | 190 | | |
| Lys | Thr | Glu | Ala | Arg | Ser | Asn | Gly | Ile | Asn | Asp | Gln | Gln | Leu | Gly | Leu |
| | | 195 | | | | | 200 | | | | | 205 | | | |
| Met | Arg | Lys | Ala | Leu | Lys | Glu | Leu | Ile | Asp | Pro | Asn | Leu | Gly | Ser | Lys |
| | 210 | | | | | 215 | | | | | 220 | | | | |
| Tyr | Ser | Asn | Lys | Thr | Pro | Ser | Gly | Tyr | Arg | Leu | Asn | Val | Phe | Glu | Ser |
| 225 | | | | | 230 | | | | | 235 | | | | | 240 |
| His | Asp | Lys | Pro | Phe | Gln | Asn | Leu | Leu | Ser | Ala | Glu | Tyr | Val | Pro | Asp |
| | | | | 245 | | | | | 250 | | | | | 255 | |
| Thr | Pro | Pro | Lys | Pro | Gly | Glu | Glu | Pro | Pro | Ala | Lys | Thr | Glu | Lys | Thr |
| | | | 260 | | | | | 265 | | | | | 270 | | |
| Ser | Val | Ile | Ile | Arg | Lys | Tyr | Ala | Glu | Gly | Asp | Ser | Lys | Leu | Leu | Glu |
| | | 275 | | | | | 280 | | | | | 285 | | | |
| Gly | Ala | Thr | Leu | Lys | Leu | Ser | Gln | Ile | Glu | Gly | Ser | Gly | Phe | Gln | Glu |
| | 290 | | | | | 295 | | | | | 300 | | | | |
| Lys | Asp | Phe | Gln | Ser | Asn | Ser | Leu | Gly | Glu | Thr | Val | Glu | Leu | Pro | Asn |
| 305 | | | | | 310 | | | | | 315 | | | | | 320 |
| Gly | Thr | Tyr | Thr | Leu | Thr | Glu | Thr | Ser | Ser | Pro | Asp | Gly | Tyr | Lys | Ile |
| | | | | 325 | | | | | 330 | | | | | 335 | |
| Ala | Glu | Pro | Ile | Lys | Phe | Arg | Val | Glu | Asn | Lys | Lys | Val | Phe | Ile | Val |
| | | | 340 | | | | | 345 | | | | | 350 | | |
| Gln | Lys | Asp | Gly | Ser | Gln | Val | Glu | Asn | Pro | Asn | Lys | Glu | Val | Ala | Glu |
| | | 355 | | | | | 360 | | | | | 365 | | | |
| Pro | Tyr | Ser | Val | Glu | Ala | Tyr | Asn | Asp | Phe | Met | Asp | Glu | Glu | Val | Leu |
| | 370 | | | | | 375 | | | | | 380 | | | | |
| Ser | Gly | Phe | Thr | Pro | Tyr | Gly | Lys | Phe | Tyr | Tyr | Ala | Thr | Asn | Lys | Asp |
| 385 | | | | | 390 | | | | | 395 | | | | | 400 |

```
Lys Ser Ser Gln Val Val Tyr Cys Phe Asn Ala Asp Leu His Ser Pro
                405                 410                 415
Pro Asp Ser Tyr Asp Ser Gly Glu Thr Ile Asn Pro Asp Thr Ser Thr
            420                 425                 430
Met Lys Glu Val Lys Tyr Thr His Thr Ala Gly Ser Asp Leu Phe Lys
        435                 440                 445
Tyr Ala Leu Arg Pro Arg Asp Thr Asn Pro Glu Asp Phe Leu Lys His
450                 455                 460
Ile Lys Lys Val Ile Glu Lys Gly Tyr Lys Lys Gly Asp Ser Tyr
465                 470                 475                 480
Asn Gly Leu Thr Glu Thr Gln Phe Arg Ala Ala Thr Gln Leu Ala Ile
            485                 490                 495
Tyr Tyr Phe Thr Asp Ser Ala Asp Leu Lys Thr Leu Lys Thr Tyr Asn
            500                 505                 510
Asn Gly Lys Gly Tyr His Gly Phe Glu Ser Met Asp Glu Lys Thr Leu
        515                 520                 525
Ala Val Thr Lys Glu Leu Ile Thr Tyr Ala Gln Asn Gly Ser Ala Pro
    530                 535                 540
Gln Leu Thr Asn Leu Asp Phe Phe Val Pro Asn Asn Ser Lys Asp Gln
545                 550                 555                 560
Ser Leu Ile Gly Thr Glu Cys His Pro Asp Asp Leu Val Asp Val Ile
            565                 570                 575
Arg Met Glu Asp Lys Lys Gln Glu Val Ile Pro Val Thr His Ser Leu
            580                 585                 590
Thr Val Lys Lys Thr Val Val Asp Glu Leu Gly Asp Lys Thr Lys Gly
        595                 600                 605
Phe Gln Phe Glu Leu Glu Leu Lys Asp Lys Thr Gly Gln Pro Ile Val
    610                 615                 620
Asn Thr Leu Lys Thr Asn Asn Gln Asp Leu Val Ala Lys Asp Gly Lys
625                 630                 635                 640
Tyr Ser Phe Asn Leu Lys His Gly Asp Thr Ile Arg Ile Glu Gly Leu
            645                 650                 655
Pro Thr Gly Tyr Ser Tyr Thr Leu Lys Glu Ala Glu Ala Lys Asp Tyr
            660                 665                 670
Ile Val Thr Val Asp Asn Lys Val Ser Gln Glu Ala Gln Ser Val Gly
        675                 680                 685
Lys Asp Ile Thr Glu Asp Lys Lys Val Thr Phe Glu Asn Arg Lys Asp
    690                 695                 700
Leu Val Pro Pro Thr Gly Leu Thr Thr Asp Gly Ala Ile Tyr Leu Trp
705                 710                 715                 720
Leu Leu Leu Leu Val Pro Leu Gly Leu Leu Val Trp Leu Phe Gly Arg
            725                 730                 735
Lys Gly Leu Lys Asn Asp
            740

<210> SEQ ID NO 5
<211> LENGTH: 509
<212> TYPE: PRT
<213> ORGANISM: Streptococcus pyogenes

<400> SEQUENCE: 5

Met Pro Tyr Val Lys Lys Lys Asp Ser Phe Leu Val Glu Thr Tyr
1               5                   10                  15

Leu Glu Gln Ser Ile Arg Asp Lys Ser Glu Leu Val Leu Leu Leu Phe
```

-continued

```
                20                  25                  30
Lys Ser Pro Thr Ile Ile Phe Ser His Val Ala Lys Gln Thr Gly Leu
         35                  40                  45
Thr Ala Val Gln Leu Lys Tyr Tyr Cys Lys Glu Leu Asp Asp Phe Phe
         50                  55                  60
Gly Asn Asn Leu Asp Thr Ile Lys Lys Gly Lys Ile Ile Cys Cys Phe
 65                  70                  75                  80
Val Lys Pro Val Lys Glu Phe Tyr Leu His Gln Leu Tyr Asp Thr Ser
                 85                  90                  95
Thr Ile Leu Lys Leu Leu Val Phe Phe Ile Lys Asn Gly Thr Ser Ser
                100                 105                 110
Gln Pro Leu Ile Lys Phe Ser Lys Lys Tyr Phe Leu Ser Ser Ser Ser
            115                 120                 125
Ala Tyr Arg Leu Arg Glu Ser Leu Ile Lys Leu Leu Arg Glu Phe Gly
        130                 135                 140
Leu Arg Val Ser Lys Asn Thr Ile Val Gly Glu Tyr Arg Ile Arg
145                 150                 155                 160
Tyr Leu Ile Ala Met Leu Tyr Ser Lys Gly Phe Ile Val Ile Tyr Pro
                165                 170                 175
Leu Asp His Leu Asp Asn Gln Ile Ile Tyr Arg Phe Leu Ser Gln Ser
                180                 185                 190
Ala Thr Asn Leu Arg Thr Ser Pro Trp Leu Glu Glu Pro Phe Ser Phe
            195                 200                 205
Tyr Asn Met Leu Leu Ala Leu Ser Trp Lys Arg His Gln Phe Ala Val
        210                 215                 220
Ser Ile Pro Gln Thr Arg Ile Phe Arg Gln Leu Lys Lys Leu Phe Ile
225                 230                 235                 240
Tyr Asp Cys Leu Thr Arg Ser Ser Arg Gln Val Ile Glu Asn Ala Phe
                245                 250                 255
Ser Leu Thr Phe Ser Gln Gly Asp Leu Asp Tyr Leu Phe Leu Ile Tyr
                260                 265                 270
Ile Thr Thr Asn Asn Ser Phe Ala Ser Leu Gln Trp Thr Pro Gln His
            275                 280                 285
Ile Glu Thr Cys Cys His Ile Phe Glu Lys Asn Asp Thr Phe Arg Leu
        290                 295                 300
Leu Leu Glu Pro Ile Leu Lys Arg Leu Pro Gln Ile Asn His Ser Lys
305                 310                 315                 320
Gln Asp Leu Ile Lys Ala Leu Met Tyr Phe Ser Lys Ser Phe Leu Phe
                325                 330                 335
Asn Leu Gln His Phe Val Ile Glu Ile Pro Ser Phe Ser Leu Pro Thr
                340                 345                 350
Tyr Thr Gly Asn Ser Asn Leu Tyr Lys Ala Leu Lys Asn Ile Val Asn
            355                 360                 365
Gln Trp Leu Ala Gln Leu Pro Gly Lys Arg His Leu Asn Glu Lys His
        370                 375                 380
Leu Gln Leu Phe Ser Cys His Ile Glu Gln Ile Leu Lys Asn Lys Gln
385                 390                 395                 400
Pro Ala Leu Thr Val Val Leu Ile Ser Ser Asn Phe Ile Asn Ala Lys
                405                 410                 415
Leu Leu Thr Asp Thr Ile Pro Arg Tyr Phe Ser Asp Lys Gly Ile His
                420                 425                 430
Phe Tyr Ser Phe Tyr Leu Leu Arg Asp Asp Ile Tyr Gln Ile Pro Ser
            435                 440                 445
```

Leu Lys Pro Asp Val Ile Thr His Ser Arg Leu Ile Pro Phe Val Lys
    450                 455                 460

Asn Asp Leu Val Lys Gly Val Thr Val Ala Glu Phe Ser Phe Asp Lys
465                 470                 475                 480

Pro Asp Tyr Ser Ile Ala Ser Ile Gln Asn Leu Ile Tyr Gln Leu Lys
            485                 490                 495

Asp Lys Lys Tyr Gln Asp Phe Leu Asn Glu Gln Leu Gln
        500                 505

<210> SEQ ID NO 6
<211> LENGTH: 19
<212> TYPE: DNA
<213> ORGANISM: Streptococcus pyogenes

<400> SEQUENCE: 6 atttttctc atgttgcta                                             19

<210> SEQ ID NO 7
<211> LENGTH: 19
<212> TYPE: DNA
<213> ORGANISM: Streptococcus pyogenes

<400> SEQUENCE: 7
gtttagaatg gtttaattg                                            19

<210> SEQ ID NO 8
<211> LENGTH: 18
<212> TYPE: DNA
<213> ORGANISM: Streptococcus pyogenes

<400> SEQUENCE: 8
gccaataact gaggtagc                                             18

<210> SEQ ID NO 9
<211> LENGTH: 19
<212> TYPE: DNA
<213> ORGANISM: Streptococcus pyogenes

<400> SEQUENCE: 9
ggcttttgct cttttaggt                                            19

<210> SEQ ID NO 10
<211> LENGTH: 20
<212> TYPE: DNA
<213> ORGANISM: Streptococcus pyogenes

<400> SEQUENCE: 10
agttcacaag ttgtctactg                                           20

<210> SEQ ID NO 11
<211> LENGTH: 20
<212> TYPE: DNA
<213> ORGANISM: Streptococcus pyogenes

<400> SEQUENCE: 11
aaataataga tagcaagctg                                           20

<210> SEQ ID NO 12
<211> LENGTH: 20
<212> TYPE: DNA
<213> ORGANISM: Streptococcus pyogenes -continued

```
<400> SEQUENCE: 12
attaatgcca gagttagatg                                              20

<210> SEQ ID NO 13
<211> LENGTH: 18
<212> TYPE: DNA
<213> ORGANISM: Streptococcus pyogenes

<400> SEQUENCE: 13
cgattctctt ccactttg                                                18

<210> SEQ ID NO 14
<211> LENGTH: 22
<212> TYPE: DNA
<213> ORGANISM: Streptococcus pyogenes

<400> SEQUENCE: 14
tactctgtta aagaagtaac tg                                           22

<210> SEQ ID NO 15
<211> LENGTH: 18
<212> TYPE: DNA
<213> ORGANISM: Streptococcus pyogenes

<400> SEQUENCE: 15
ctcagagtca ctttctgg                                                18

<210> SEQ ID NO 16
<211> LENGTH: 19
<212> TYPE: DNA
<213> ORGANISM: Streptococcus pyogenes

<400> SEQUENCE: 16
ggattttgcc tactactta                                               19

<210> SEQ ID NO 17
<211> LENGTH: 20
<212> TYPE: DNA
<213> ORGANISM: Streptococcus pyogenes

<400> SEQUENCE: 17
gtggaatatc taaaacagac                                              20

<210> SEQ ID NO 18
<211> LENGTH: 23
<212> TYPE: DNA
<213> ORGANISM: Streptococcus pyogenes

<400> SEQUENCE: 18
ttttattgga gactagaagt tta                                          23

<210> SEQ ID NO 19
<211> LENGTH: 18
<212> TYPE: DNA
<213> ORGANISM: Streptococcus pyogenes

<400> SEQUENCE: 19
agcaagccac tgatttac                                                18

<210> SEQ ID NO 20
<211> LENGTH: 19
<212> TYPE: DNA
<213> ORGANISM: Streptococcus pyogenes
```

```
<400> SEQUENCE: 20
tgcaaaagag ggataaaac                                             19

<210> SEQ ID NO 21
<211> LENGTH: 20
<212> TYPE: DNA
<213> ORGANISM: Streptococcus pyogenes

<400> SEQUENCE: 21
gaagcagtag acaacttgtg                                            20

<210> SEQ ID NO 22
<211> LENGTH: 20
<212> TYPE: DNA
<213> ORGANISM: Streptococcus pyogenes

<400> SEQUENCE: 22
taaactaaag tagcttagca                                            20

<210> SEQ ID NO 23
<211> LENGTH: 18
<212> TYPE: DNA
<213> ORGANISM: Streptococcus pyogenes

<400> SEQUENCE: 23
atggaacgtc atcacaac                                              18

<210> SEQ ID NO 24
<211> LENGTH: 20
<212> TYPE: DNA
<213> ORGANISM: Streptococcus pyogenes

<400> SEQUENCE: 24
cagataccta aaaataaacg                                            20

<210> SEQ ID NO 25
<211> LENGTH: 21
<212> TYPE: DNA
<213> ORGANISM: Streptococcus pyogenes

<400> SEQUENCE: 25
gctgaagaac aatcagtacc a                                          21

<210> SEQ ID NO 26
<211> LENGTH: 24
<212> TYPE: DNA
<213> ORGANISM: Streptococcus pyogenes

<400> SEQUENCE: 26
ttagtcattt tttaaccctt tacg                                       24

<210> SEQ ID NO 27
<211> LENGTH: 22
<212> TYPE: DNA
<213> ORGANISM: Streptococcus pyogenes

<400> SEQUENCE: 27
ctttttactt attaagagat ga                                         22

<210> SEQ ID NO 28
<211> LENGTH: 18
<212> TYPE: DNA
```

```
<213> ORGANISM: Streptococcus pyogenes

<400> SEQUENCE: 28
ctcgtttaga aaatcttg                                                 18

<210> SEQ ID NO 29
<211> LENGTH: 21
<212> TYPE: DNA
<213> ORGANISM: Streptococcus pyogenes

<400> SEQUENCE: 29
aaaataatta aatcaatagc a                                             21

<210> SEQ ID NO 30
<211> LENGTH: 17
<212> TYPE: DNA
<213> ORGANISM: Streptococcus pyogenes

<400> SEQUENCE: 30
ccacagagat aatgtgt                                                  17

<210> SEQ ID NO 31
<211> LENGTH: 36
<212> TYPE: DNA
<213> ORGANISM: Escherichia coli

<400> SEQUENCE: 31
gacgatctcg aggaggtaaa tgaagacgcc aaaaac                             36

<210> SEQ ID NO 32
<211> LENGTH: 31
<212> TYPE: DNA
<213> ORGANISM: Escherichia coli

<400> SEQUENCE: 32
gacgataagc ttttacaatt tggactttcc g                                  31
```

COLLAGEN-BINDING PROTEINS FROM *STREPTOCOCCUS PYOGENES*

This application is a divisional of U.S. application Ser. No. 09/494,297, filed Jan. 31, 2000 now U.S. Pat. No. 6,777,547.

FIELD OF THE INVENTION

The present invention relates in general to proteins from group A Streptococci (GAS) Fat can bind collagen, and in particular to collagen-binding proteins designated Cpa1 and Cpa49, and the nucleic acid sequences coding for those proteins, which have been isolated from *Streptococcus pyogenes* and which can be used in methods to inhibit collagen binding and thus treat or prevent infectious diseases caused by group A *Streptococcus* bacteria.

BACKGROUND OF THE INVENTION

The Streptococci bacteria are a pathogenic genera of microorganisms which have been associated with a wide variety of infectious disorders including suppuration, abscess formation, a variety of pyogenic infections, and septicemia. In particular, *Streptococcus pyogenes* (a group A streptococci, or GAS) is a prominent pathogen which causes skin and mucous membrane infections, as well as deep-seated connective tissue infections and severe, sometimes fatal, septicemia. Like many other pathogens, in order to infect the human host successfully, GAS must have the ability to adjust the expression of its virulence factors according to the varying conditions of different anatomical sites.

In GAS, the expression of several virulence factors is positively regulated at the level of transcription by the Mga regulator. See Perez-Casal et al. (1991); Chen et al., 1993; Podbielski et al. (1995) and (1996). Regulated genes include M and M-related proteins (phagocytosis resistance, eukaryotic cell interactions), fibronectin-related proteins (serum opacity factor). Speβ (protease) and c5a peptidase (inactivation of complement factor c5a). Recent evidence has demonstrated that, in addition to iron levels, pH, $CO_2$, and temperature (see Caparon et al., 1992; Podbielski et al., 1992; Okada et al., 1993; McIver et al., 1995) and activity of the Mga regulator is associated with logarithmic and late logarithmic growth phase. See McIver et al. (1997).

Another regulator in *Streptococcus* is RofA, a positive transcriptional regulator of the fibronectin-binding protein (prtF) (see Fogg et al., 1994 and 1997) that promote bacterial attachment to the host extracellular matrix (see Hanski et al., 1992; and Van Heyningen et al., 1993). In contrast to Mga-controlled genes, RofA positively regulates prtF transcription as well as its own transcription in response to increased levels of $O_2$. By a potentially independent mechanism, transcription of prtF is also induced in response to intracellular superoxide levels (see Gibson et al., 1996).

These data have suggested differential expression of eukaryotic cell-binding proteins such as RofA-dependent prtF and Mga-dependent emm in response to $O_2$ and $CO_2$ partial pressures. These observations have led to the proposal that these regulators may influence the expression of proteins important for the attachment of GAS in different in vivo environments such as superficial Langerhans cells or subsurface keratinocytes (Okada et al. 1994; 1995). As has been observed with regard to other bacterial species, the attachment of bacteria to host cells or implanted biomaterials is generally initiated through "extracellular matrix proteins," or ECM's, which generally refer to such general families of macromolecules, collagens, structural glycoproteins, proteoglycans and elastins, including fibronectin, and fibrinogen, that provide support and modulate cellular behavior. However, the precise role of the bacteria's ability to bind to these extracellular matrix proteins and the knowledge of how to best utilize this information in order to prevent streptococcal infection has not yet been fully determined.

Moreover, outside of the two regulators RofA and Mga, very little is known with regard to environmentally dependent virulence gene expression in GAS, and thus there has been very limited information with regard to the regulation and inhibition of the extracellular matrix proteins that are responsible for the attachment and infection caused by GAS. In light of the extremely severe nature of the bacterial infections caused by the Streptococcal bacteria, it is extremely important to make a determination of which specific proteins are responsible for attachment to the surface of targeted cells, and to be able to use this information in order to develop vaccines and other biological agents which can be used to treat or prevention the severe infections associated with group A streptococci.

SUMMARY OF THE INVENTION

Accordingly, it is an object of the present invention to provide isolated proteins (adhesins) from group A streptococci which can bind to intercellular matrix proteins such as collagen so as to be useful in developing methods of inhibiting collagen binding and attachment of streptococcal bacteria to cells.

It is a further object of the present invention to provide isolated streptococcal surface proteins that are able to inhibit adhesion to the immobilized extracellular matrix or host cells present on the surface of implanted biomaterials.

It is a further object of the present invention to provide a vaccine which can be used in treating or preventing infection by group A streptococcal bacterial such as *Streptococcus pyogenes*.

It is still further an object of the present invention to generate antisera and antibodies to the collagen binding proteins from GAS which can also be useful in developing methods of treatment which can inhibit binding of the streptococcal bacteria to host cells or to implanted biomaterials and thus be employed in order to treat or prevent Streptococcal infection.

It is a further object of the present invention to provide improved materials and methods for detecting and differentiating collagen-binding proteins in streptococcal organisms in clinical and laboratory settings.

It is a further object of the invention to provide nucleic acid sequences which code for the collagen binding proteins in GAS which can also be useful in producing the collagen-binding proteins of the invention and in developing probes and primers specific for identifying and characterizing these proteins.

These and other objects are provided by virtue of the present invention which comprises isolated collagen binding proteins from group A streptococcal bacteria such as *Streptococcus pyogenes* along with their amino acid and nucleic acid sequences. Two of the specific proteins isolated in accordance with the invention are designated Cpa1 and Cpa49 which are obtained from the collagen binding region in *Streptococcus pyogenes*, and the sequences for those proteins are those as shown in SEQ ID NOS. 2 and 4, respectively. The nucleic acid sequences coding for Cpa1 and Cpa49 are shown in SEQ ID NOS. 1 and 3, respectively. The isolated proteins of the present invention have been observed to bind to collagen, and thus can be utilized in methods of treating or preventing streptococcal infection through the inhibition of the ability of the bacteria to bind to collagen.

In another aspect of the present invention, there is also provided antisera and antibodies generated against the collagen binding proteins of the present invention which also can be utilized in methods of treatment which involve inhibition of the attachment of the Cpa proteins to collagen. In particular, specific polyclonal antiserum against Cpa has been generated which has been shown to react with Cpa in Western immunoblots and ELISA assays and which interferes with Cpa binding to collagen. This antiserum can thus be used for specific agglutination assays to detect bacteria which express Cpa on their surface. The antiserum apparently does not cross-react with bacteria which express the fibronectin-binding protein F1 on their surface despite the fact that a portion of protein F1 exhibits sequence homologies to Cpa1 and Cpa49.

Accordingly, in accordance with the invention, antisera and antibodies raised against the Cpa1 and Cpa49 proteins, or portions thereof, may be employed in vaccines, and other pharmaceutical compositions containing the proteins for therapeutic purposes are also provided herein. In addition, diagnostic kits containing the appropriate nucleic acid molecules, the Cpa1 or Cpa49 proteins, or antibodies or antisera raised against them are also provided so as to detect bacteria expressing these proteins.

These embodiments and other alternatives and modifications within the spirit and scope of the disclosed invention will become readily apparent to those skilled in the art from reading the present specification and/or the references cited herein.

BRIEF DESCRIPTION OF THE DRAWING FIGURES

FIG. 1 is a schematic representation of a comparison of the nra (SEQ ID NO. 5)/rofA-associated portions of group A streptococcal serotype M1, M6 and M49 strains. Results of pairwise comparisons of the deduced amino acid sequences of single ORF's are shown as percentage identity values between corresponding sequences. Sequence alignments were centered at the nra (SEQ ID NO. 5)/rofA to prtF/cpa intergenic regions. All sequences are shown to scale. For designation of ORF's, see Table 1 hereinbelow. The M1 sequence was obtained from the GAS sequencing project (Roe et al., 1997), and the M6 sequence was taken from Hanski et al. (1992) and Fogg et al. (1994). The inserted box contains the comparison of the deduced Nra and RofA amino acid sequences. "." marks identical amino acid positions; "-" marks gaps that were introduced into the RofA sequence to maximize alignment. The underlined sequence marks the potential helix-turn-helix identified by Fogg et al. (1997).

Figure 2A:
Figure 2C:
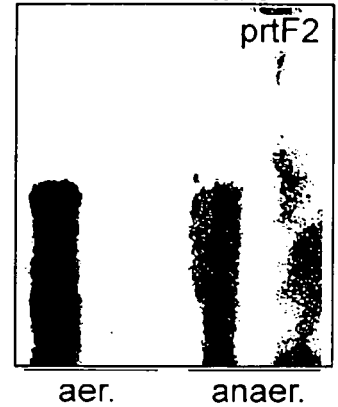
Figure 2B:
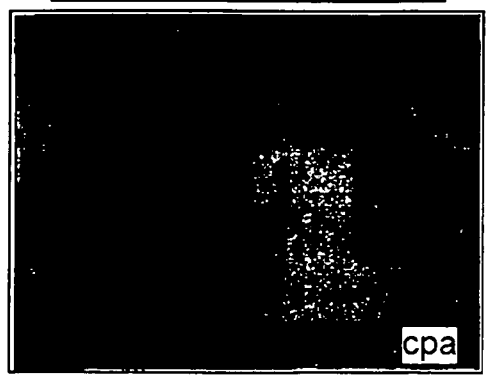

FIG. 2 depicts transcript analysis of nra and nra-regulated genes in a CAS wild-type (wt) and nra mutant (nra) strain. Total RNA was isolated from late log phase cells grown under anaerobic (aer.) and anaerobic (anaer.) conditions. Unless otherwise indicated, 20 µg of total RNA was used per lane for Northern blotting. PCR-amplified and digoxigenin-labelled probes specific for nra, cpa, nifR3L and prtF (Table 4) were used for hybridization. Northern analyses represent the results of transcription analysis of (1) the nra gene as shown in FIG. 2A, (2) operons adjacent to the nra gene as shown in FIG. 2B, and (3) the prtF gene, which is located at an unknown distance from nra, as shown in FIG. 2C. In all cases, an increase in band intensity was observed using total RNA isolated from the nra mutant. With the exception of cpa, this increase was particularly pronounced in RNA prepared from anaerobically grown cultures. The nra message in the wild-type strain was expressed at very low and sometimes undetectable levels.

Figure 3:
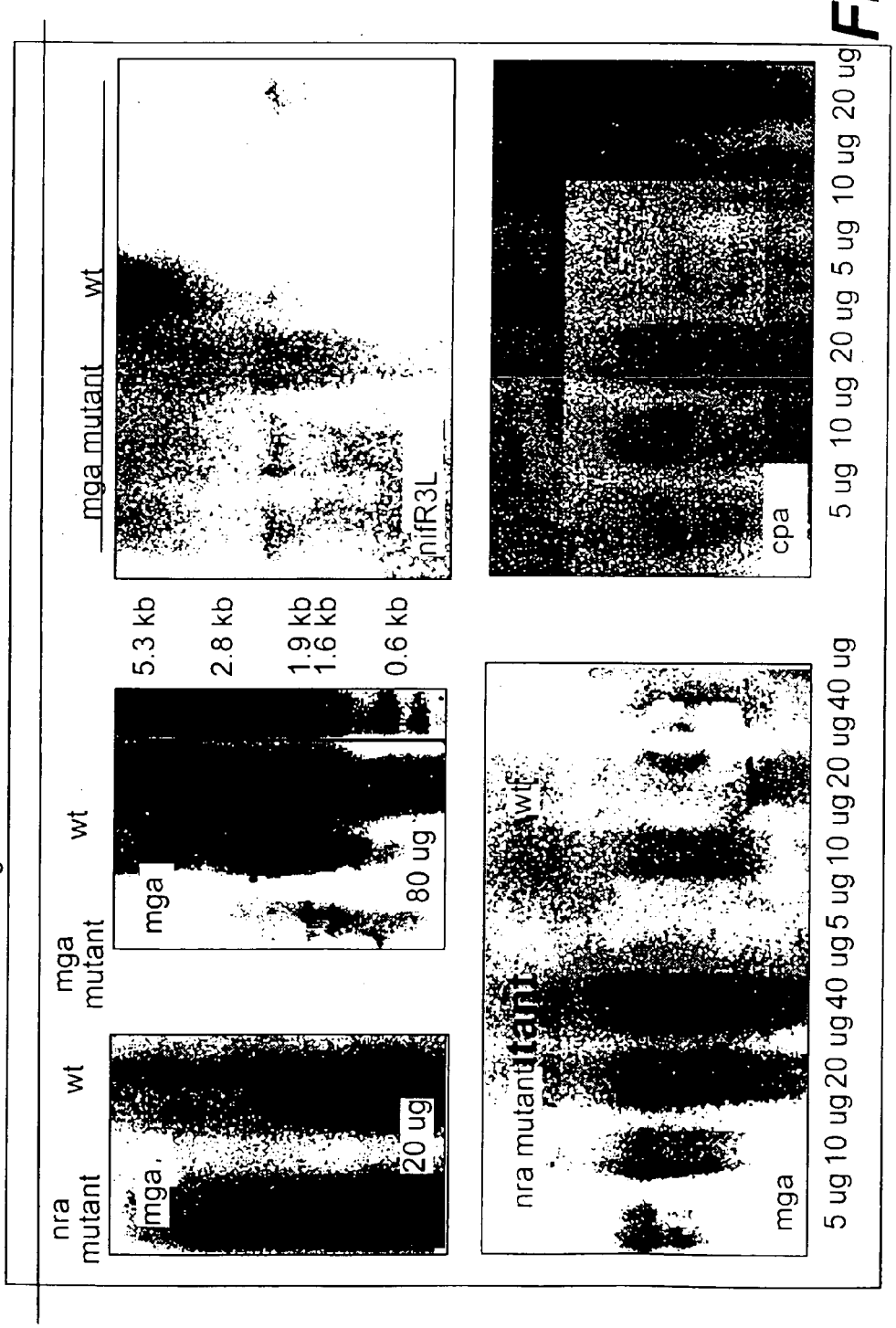

FIG. 3 depicts transcript analysis of the positive global mga regulator gene in GAS wild-type (wt) and nra mutant strains, and the transcript analysis of nra, nifR3L and cpa in GAS wild-type (wt) and mga mutant strains. Total RNA was prepared from mid-log phase cells grown under anaerobic conditions and was subjected to Northern blot hybridization using the indicated RNA amounts per lane. PCR-amplified and digoxigenin-labelled probes specific for mga and nra (left) or nifR3L and cpa (right) were used for hybridization and subsequent CSPD visualization.

Figure 4:
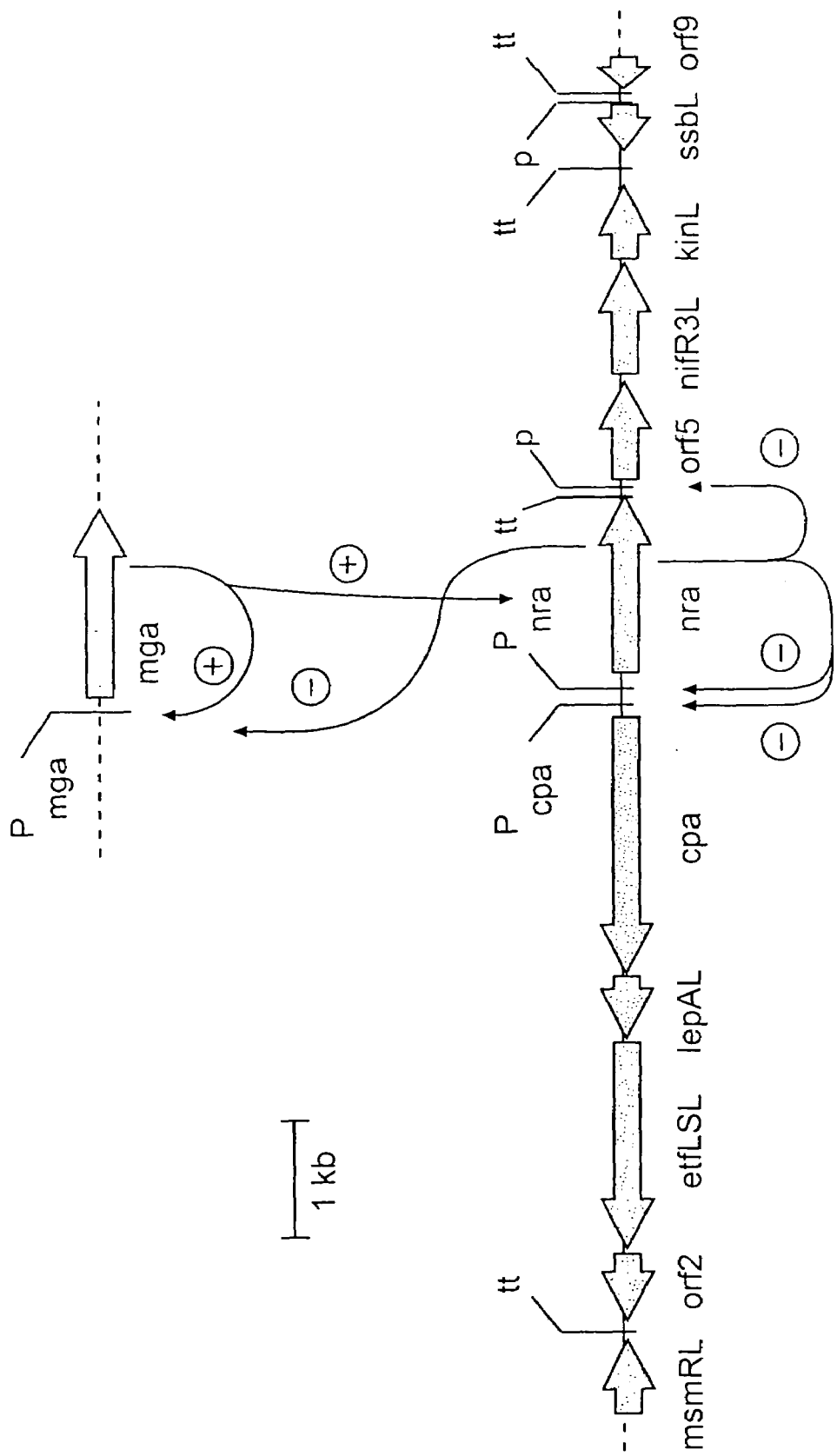

FIG. 4 is a diagram of transcription and control of nra and nra-regulated genes. Nra exhibits negative regulation (–) of its own expression, that of two adjacent operons and of the mga regulator gene. Mga is a positive regulator (+) of its own expression and that of nra. Promoters (p) and transcription terminators (tt) are shown in italics. For designation of ORFs, see Table 1. The sequences are drawn to scale.

Figure 5:
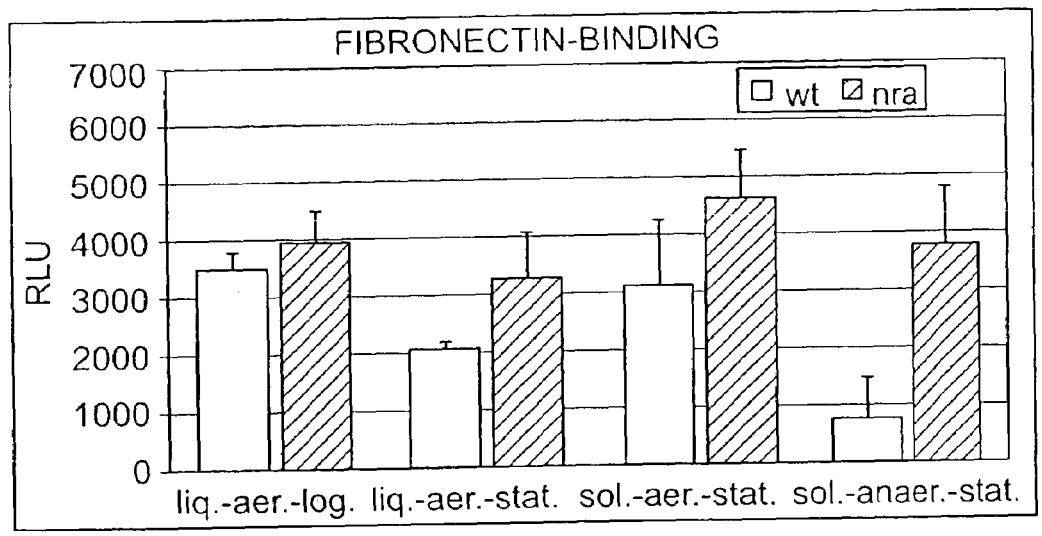
Figure 5:
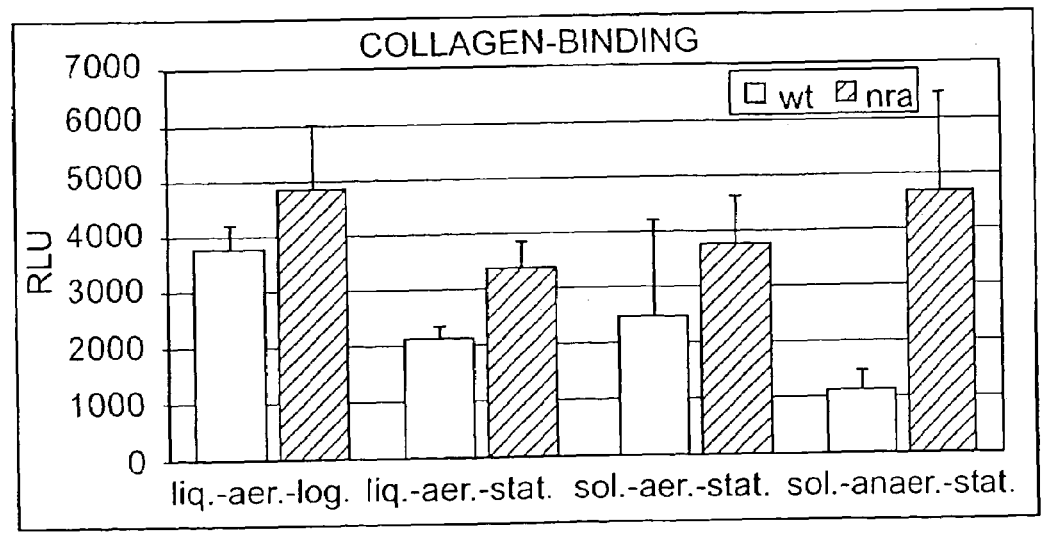

FIG. 5 depicts attachment of Gas wild-type and nra mutant strains to immobilized human fibronectin and type I collagen. The bacteria were cultured on solid THY medium under anaerobic conditions until they reached stationary phase and were then harvested for binding assays. After FTIC labeling of the cells, adherent cells were detected by measuring the relative light units (RLU) present in each sample. Normalization of the values was performed as indicated below in the Examples section.

DETAILED DESCRIPTION OF THE PREFERRED EMBODIMENTS

In accordance with the present invention, there is provided isolated collagen binding proteins from group A streptococcal bacteria, and their corresponding amino acid and nucleic acid sequences are described herein. Two specific proteins isolated in accordance with the present invention are designated Cpa1, having the nucleic acid sequence as shown in SEQ ID NO. 1 and the amino acid sequence of SEQ ID NO. 2, and Cpa49, which has the nucleic acid sequence as shown in SEQ ID NO. 3 and the amino acid sequence observed in SEQ ID No. 4. Using different experimental approaches, it has now been shown that Cpa1 and Cpa49 both bind to collagen, e.g., via binding of soluble 125-iodine labeled collagen, inhibition of binding to immobilized collagen by recombinant purified Cpa1 protein and by specific antisera directed to Cpa49/Cpa1, and thus these proteins or their antibodies can thus be useful in the treatment and prevention of group A streptococcal disease, or in techniques to identify such proteins, as described further below. It has also been determined via collagen binding experiments with recombinant purified Cpa-fragments, that the collagen binding domain can be deduced to reside in the third (C-terminal) quarter of the protein.

In addition to the structures of Cpa1 and Cpa49 as shown in the amino acid sequences of SEQ ID NOS. 2 and 4, respectively, as would be recognized by one of ordinary skill in the art, modification and changes may be made in the structure of the peptides of the present invention and DNA segments which encode them and still obtain a functional molecule that encodes a protein or peptide with desirable characteristics. The amino acid changes may be achieved by changing the codons of the DNA sequence. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In addition, amino acid substitutions are also possible without affecting the collagen binding ability of the isolated proteins of the invention, provided that the substitutions provide amino acids having sufficiently similar properties to the ones in the original sequences.

Accordingly, acceptable amino acid substitutions are generally therefore based on the relative similarity of the amino acid side in substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. The isolated proteins of the present invention can be prepared in a number of suitable ways known in the art including typical chemical synthesis processes to prepare a sequence of polypeptides.

The synthetic polypeptides of be invention can thus be prepared using the well known techniques of solid phase, liquid phase, or peptide condensation techniques, or any combination thereof, can include natural and unnatural amino acids. Amino acids used for peptide synthesis may be standard Boc ($N^{\alpha}$-amino protected $N^{\alpha}$-t-butyloxycarbonyl) amino acid resin with the standard deprotecting, neutralization, coupling and wash protocols of the original solid phase procedure of Merrifield (*J. Am. Chem. Soc.,* 85:2149–2154, 1963), or the base-labile $N^{\alpha}$-amino protected 9-fluorenylmethoxycarbonyl (Fmoc) amino acids first described by Carpino and Han (*J. Org. Chem.,* 37:3403–3409, 1972). Both Fmoc and Boc $N^{\alpha}$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^{\alpha}$-protecting groups that are familiar to those skilled in this art. Solid phase peptide synthesis may be accomplished by techniques familiar to those in the art and provided, for example, in Stewart and Young, 1984, *Solid Phase Synthesis*, Second Edition, Pierce Chemical Co., Rockford, Ill.; Fields and Noble, 1990, *Int. J. Pept Protein Res.* 35:161–214, or using automated synthesizers, such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In a further embodiment, subunits of peptides that confer useful chemical and structural properties will be chosen. For example, peptides comprising D-amino acids will be resistant to L-amino acid-specific proteases in vivo. In addition, the present invention envisions preparing peptides that have more well defined structural properties, and the use of peptidomimetics and peptidomimetic bonds, such as ester bonds, to prepare peptides with novel properties. In another embodiment, a peptide may be generated that incorporates a reduced peptide bond, i.e., $R_1$—$CH_2$—$NH$—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown or protease activity. It is also well known that in certain systems, constrained peptides show enhanced functional activity (Hruby, *Life Sciences,* 31:189–199, 1982); (Hruby et al., *Biochem J.,* 268:249–262, 1990).

Also provided herein are sequences of nucleic acid molecules that selectively hybridize with nucleic acid molecules encoding the collagen-binding proteins of the invention, or portions thereof, such as consensus or variable sequence amino acid motifs, from *Streptococcus pyogenes* described herein or complementary sequences thereof. By "selective" or "selectively" is meant a sequence which does not hybridize with other nucleic acids. This is to promote specific detection of Cpa1 or Cpa49. Therefore, in the design of hybridizing nucleic acids, selectivity will depend upon the other components present in a sample. The hybridizing nucleic acid should have at least 70% complementarity with the segment of the nucleic acid to which it hybridizes. As used herein to describe nucleic acids, the term "selectively hybridizes" excludes the occasional randomly hybridizing nucleic acids, and thus, has the same meaning as "specifically hybridizing". The selectively hybridizing nucleic acids of the invention can have at least 70%, 80%, 85%, 90%, 95%, 97%, 98%, and 99% complementarity with the segment of the sequence to which they hybridize.

The invention contemplates sequences, probes and primers which selectively hybridize to the encoding DNA or the complementary, or opposite, strand of DNA as those specifically provided herein. Specific hybridization with nucleic acid can occur with minor modifications or substitutions in the nucleic acid, so long as functional species-specific hybridization capability is maintained. By "probe" is meant nucleic acid sequences that can be used as probes or primers for selective hybridization with complementary nucleic acid sequences for their detection or amplification, which probes can vary in length from about 5 to 100 nucleotides, or preferably from about 10 to 50 nucleotides, or most preferably about 18–24 nucleotides. Therefore, the terms "probe" or "probes" as used herein are defined to include "primers". Isolated nucleic acids are provided herein that selectively hybridize with the species-specific nucleic acids under stringent conditions and should have at least 5 nucleotides complementary to the sequence of interest as described by Sambrook et al., 1989. MOLECULAR CLONING: A LABORATORY MANUAL, 2nd ed. Cold Spring Harbor Laboratory, Cold Spring Harbor, N.Y.

If used as primers, the composition preferably includes at least two nucleic acid molecules which hybridize to different regions of the target molecule so as to amplify a desired region. Depending on the length of the probe or primer, the target region can range between 70% complementary bases and full complementarity and still hybridize under stringent conditions. For example, for the purpose of diagnosing the presence of the *S. pyogenes*, the degree of complementarity between the hybridizing nucleic acid (probe or primer) and the sequence to which it hybridizes (e.g., group A streptococcal DNA from a sample) is at least enough to distinguish hybridization with a nucleic acid from other bacteria.

The nucleic acid sequences encoding Cpa1 or Cpa49 proteins or portions thereof, such as consensus or variable sequence amino acid motifs, can be inserted into a vector, such as a plasmid, and recombinantly expressed in a living organism to produce recombinant Cpa1 or Cpa49 proteins or active fragments thereof.

Recombinant proteins are produced by methods well known to those skilled in the art. A cloning vector, such as a plasmid or phage DNA is cleaved with a restriction enzyme, and the DNA sequence encoding the Cpa1 or Cpa49 protein or active fragments thereof, such as consensus or variable sequence amino acid motifs, is inserted into the cleavage site and ligated. The cloning vector is then inserted into a host to produce the protein or fragment encoded by the Cpa1 or Cpa49 encoding DNA. Suitable hosts include bacterial hosts such as *Escherichia coli*, *Bacillus subtilis*, yeasts and other cell cultures. Production and purification of the gene product may be achieved and enhanced using known molecular biology techniques.

In accordance with the present invention, we have sequenced an 11.5 kb genomic fragment of serotype M49 GAS strain CS101 harboring the nra gene that is 63% homologous to the rofA positive regulatory gene. In contrast to the apparent function of rofA, nra was found to encode a negative regulator affecting its own expression, the expression of two adjacent operons and several other genes. Some of these genes encode potentional intracellular proteins, whereas others encode surface proteins such as the collagen-binding CPA (this study) and the fibronectin-binding PrtF2 (Jaffe et al., 1996), which may be involved in virulence In addition, nra influences the expression of the mga regulatory gene and, thereby, the factors contained in the mga region. Expression of nra was found to be maximal in early stationary phase and was not significantly influenced by atmospheric conditions. Overall, the present invention includes the identification of a unique GAS negative regulator and implicates its function in a regulatory network affecting virulence factor expression in GAS, as set forth in detail in Podbielski et al., *Molecular Microbiol.* 31(4):1051–1064 (1999), incorporated herein by reference.

In accordance with the present invention, an analysis was undertaken of the genomic region containing the nra gene. In this analysis, an 11 489 bp portion of the GAS chromosome was sequenced from a Lambda library of the serotype M49 GAS genome (GenBank accession no. U 49397). Computer analysis of this sequence revealed the present of nine complete and two partial predicted open reading frames (ORFs) (FIG. 1). Homology comparisons with GenBank entries demonstrated the similarity of 10 of the ORFs to known bacterial protein sequences (Table 1). Detailed analysis of the gene products encoded in this region (see the following sections) revealed the presence of a negative regulatory gene, nra, and immediately upstream in the opposite orientation, a collagen-binding protein, cpa. The genomes of GAS serotypes in GenBank and the available streptococcal serotype M1 genomic sequences (Roe et al., 1997) were searched for homologues to nra and cpa (FIG. 1). The gene sharing the highest degree of homology with nra was the positive regulatory factor, rofA, while cpa showed the highest homology to a gene for a fibronectin-binding protein, prtF.

A more detailed computer analysis of the similarity between the negative regulator nra and the positive regulator rofA showed that both contain similar N-terminal double helix-turn-helix motifs (FIG. 1) whose intramolecular localization would be consistent with a negative or dual regulatory function of the proteins (Prag et al., 1997). Homology between the collagen-binding cpa genes and the fibronectin-binding prtF genes was confined to the N-terminal sections and did not include the portions of prtF encoding its two fibronectin binding domains (Taley et al., 1994; Ozeri et al., 1996; Sela et al., 1993). The genes of fibronectin-binding proteins F have at least two isotypes, prtF (Hanski and Caparon, 1992) and sfb (Talay et al., 1992), which exhibit 52% sequence homology. Similarly the genes of collagen-binding proteins, cpa, also appeared to have multiple forms such as cps in M49 and cpa.1 in M1, which shared approximately 53% homology to each other and 23% homology to the prtF family of proteins.

In order to confirm and extend the results of the sequence comparisons, oligonucleotides specific for prtF (Natanson et al., 1995), prtF2, cpa (M49/M1), nra and rofA genes (Table 4) were synthesized. These oligonucleotides were used as polymerase chain reaction (PCR) primers on genomic DNA from serotypes M1, M2, M3, M4, M5, M6, M12, M18, M24 (Table 2) and eight independent M49 strains. In addition, the primers were used to generate probes for Southern blot hybridizations that were performed with EcoRI- and HindiII-digested genomic DNA of the 10 serotype strains (Table 2). Based on the results from both analyses, no variation was found within the M49 serotype. However, different M protein serotype strains harbored either rofA, nra or both genes. Any combination of regulator and binding protein (cpa, prtF, prtF2) could also be found. Therefore, the nra/cpa and rofA/prtF pairs are not mutually exclusive, and single strains can also contain any combination of regulators and binding proteins. What was particularly striking was that, although M49- and M1-contained gene pairs had different regulatory proteins (cpa/nra and cpa.1/rofA.1 respectively), the binding and regulatory genes were flanked by five genes sharing >98% homology and three genes with <50% homology that indicated that cpa and nra could be part of a pathogenicity island. In the serotype M49 strain used for further study, in addition to the cpa/nra gene pair, a prtF2 gene was contained in a separate location on the GAS chromosome. The localization of other regulator/binding protein pairs, especially in strains containing multiple regulators or binding proteins, awaits further analysis.

The transcriptional organization of nra, cpa and flanking genes was determined by Northern blotting using PCR-generated specific probes (see Table 4 for primer sequences). Each Northern blot was repeated three or four times, and the results are given in FIG. 2. To determine the effect of nra on the transcription of itself and neighboring genes, an nra mutant was constructed by genomic insertion of the plasmid pFW11. The construct was confirmed by Southern blot hybridization and specific PCRs using nra mutant genomic DNA (data not shown). As transcription of rofA, the gene sharing the greatest homology to nra, is increased under aerobic conditions, the Northern analyses were carried out on RNA isolated from cells grown under both aerobic and anaerobic conditions. It should be noted that nra was transcribed at very low rates and was barely detectable in 80 µg of total RNA.

The nra region was found to be monocistronically transcribed (≈1.8 kb) and upregulated in an nra mutant. Transcription was slightly, although probably not significantly, induced under aerobic conditions (FIG. 2A). The three genes immediately downstream of nra, ORF5-nifR3L-kinL, were transcribed as an operon whose 2.6 kb transcript, as detected with a nifR3L probe, is shown in FIG. 2B. The ORF5-kinL operon was expressed at higher levels under aerobic conditions and in an nra mutant, suggesting that this operon falls under the control of nra. The different transcription rates of nifR3L in wild-type and nra mutant strains were confirmed by Northern blots performed on serial dilutions of total mRNA (FIG. 2B). Reverse transcriptase (RT)-PCR carried out on total mRNA using primers directed to the 3' end of nra and the 5' end of ORF5 yielded a product that would be present only if at least some transcriptional readthrough occurs between nra and ORF5 (data not shown). Thus, inverted repeats present in the non-coding section between nra and ORF5 serve only as a weak transcriptional terminator, allowing a small amount of readthrough between nra and ORF5. However, the majority of the nifR3L transcript originates from a second promoter upstream of ORF5, as only the ORF5-kinL transcript could be visualized on the Northern blots. Because insertion of pFW11 in nra disrupted readthrough between nra and ORF5, the only promoter still present in the nra mutants was the promoter ahead of ORF5. As the ORF5-kinL product was still increased in the nra mutants, it indicates that nra also has a negative regulatory effect at the promoter immediately upstream of ORF5.

Northern analyses using a cpa probe detected a 5.2 kb transcript composed of the four (cpa-ORF2) located immediately upstream of and in the opposite orientation to nra (FIG. 2B). Transcription of the cpa operon was also increased in an nra mutant, suggesting its regulation by nra. However, unlike the nra and ORF5-kinL transcripts, the cpa-ORF2 transcript was more abundant under anaerobic conditions, subsiding a possible superimposed second regulatory mechanism for this operon.

Northern blots using a prtF2 probe detected an mRNA consistent in size with a monocistronic transcription of prtF2 (FIG. 2C). Although the gene is located at a distant site in the chromosome, increased transcription of an nra mutant was detected, and its expression is increased under aerobic conditions. However, the effects of nra mutation did not generally influence mRNA transcription rate or stability, as the recA transcript was not affected in the nra mutant (data not shown).

As nra appeared to be a global negative regulator of virulence factors. Northern blots were used to determine whether nra and the global positive virulence factor regulator mga (FIG. 3) affected each other. Levels of mga mRNA were increased in the nra mutant (Podbielski et al., 1995) for Northern blot analysis, the nra message was found to be decreased in the mga mutant, which led to a corresponding increase in the nifR3L and cpa transcripts that are negatively regulated by nra (FIG. 3).

Taken together, the data from the different transcript analyses indicate that the nra gene product is a negative regulator of its own expression and the two adjacent operons as well as of prtF2 and mga (FIG. 4). The mga regulator, in turn, was suggested to be a positive regulator of nra expression and, thus, an indirect suppressor of nra-dependent genes (FIG. 4).

With regard to the gene coding for the collagen-binding region of the group A streptococci, the cpa gene was demonstrated to be negatively regulated by the nra gene product. To determine whether CPA was involved in matrix molecule interactions, a recombinant CPA-maltose binding protein fusion was expressed in *Escherichia Coli*. After purification and labeling, it was subjected to an enzyme-linked binding assay with the Immobilized human matrix proteins, collagen type 1, fibronectin and laminin. Using the purified maltose-binding protein as a negative control, the Cpa-fusion protein bound significantly to collagen and, to a lesser extent, to laminin ($P<0.05$ as determined by the Wilcoxon range test) (Table 3). Binding of Cpa to fibronectin and BSA remained at the level of the maltose-binding protein alone. Thus, like protein F2, Cpa is a second nra-controlled, potential GAS surface protein, exhibiting human matrix protein-binding properties.

The regulation of these binding proteins by nra would predict that stationary phase M49 nra mutants may still contain Cpa and protein F2, as they continue to transcribe cpa and prtF2 upon entry into stationary phase. This could result in better fibronectin and collagen binding by stationary phase nra mutants. To test this prediction, M49 wild type and nra mutant strains were cultured on plates under anaerobic conditions until stationary phase was reached. The cells were harvested, fluorescein isothiocyanate (FITC) labeled and the binding of the two strains to immobilized collagen and fibronectin was measured. The nra mutant exhibits significantly increased binding to both matrix proteins compared with the wild type (FIG. 5). Collagen-binding assays conducted with unmarked cells that were detected with labeled polyclonal serum yielded similar results (data not shown), suggesting that the FITC-labeling protocol did not damage the cells or alter binding significantly. As recombinant Cpa was found to block the binding of FITC-labeled GAS to immobilized collagen (data not shown), the binding of cells to collagen is probably mediated through the interaction of Cpa and collagen. Overall, these data indicate that, while wild-type bacteria could decrease their affinity to matrix proteins when entering stationary growth phase, the nra mutants no longer had this ability.

The organization of the genomic regions controlled by nra were remarkably similar to those flanking rofA (FIG. 1). The five downstream genes were more than 98% homologous. The upstream four-gene operon structure was conserved for both regulators. However, the homology of these genes was only 43–52% across serotypes. In rofA-containing M6, the first gene upstream was the fibronectin-binding protein gene, prtF. In the rofA-containing serotype M1 and the nra-containing serotype M49, the first gene of the upstream operon consisted of a novel gene, cpa. Protein purification and binding studies showed that cpa encoded a collagen-binding protein that was unable to bind fibronectin. Further PCR and Southern hybridization analysis of other GAS M serotypes confirmed that there was no correlation between the regulator (nra/rofA) and the binding protein contained in the upstream operon (prtF/cpa). In addition, strains were found that contained both regulators and/or multiple binding proteins. For example, serotype M49 contained an nra/cpa pair. However, a prtF2 gene located elsewhere in the chromosome was monocistronically transcribed and still negatively regulated by nra. The presence of both the positive rofA regulator and the negative nra regulator in the serotype M5 and the presence of only rofA in serotype M6 may explain the Influences of genomic background noted during studies of RofA regulation in these serotypes (Van Heyningen et al., 1993; Fogg and Caparon, 1997).

The expression of nra during growth was followed using a luciferase reporter gene fused to the 3' end of nra. The high-sensitivity detection of luciferase activity by a luminometer coupled with the 10 min half-life of luciferase in GAS (unpublished results) allowed the analysis of luc-fusion activity even at low cell densities nra was transcribed at the highest rate during early stationary phase and was not significantly influenced by atmospheric conditions. This was in contrast to rofA, which has been described as being maximally active under aerobic conditions (Fogg and Caparon, 1997). The differences in these results could reflect either differences in sensor capacity between rofA and nra or a methodological difference in the assay methods used. The rofA measurements were done by determining the level of an accumulated stable β-galactosidase reporter from a multicopy plasmid obtained using the experimental procedures described in the examples below.

In addition to the Cpa proteins above in various procedures, including the detection of the presence of Cpa1 or Cpa49 or their antibodies, the present invention also contemplates the use of the nucleic acids described herein to detect and identify the presence of collagen-binding GAS as well. The methods are useful for diagnosing group A streptococcal infections and other streptococcal diseases such as may occur in catheter related infections, biomaterial related infections, respiratory tract infections, cardiac, gastrointestinal or central nervous system infections, ocular infections, wound infections, skin infections, and a myriad of other diseases including conjunctivitis, keratitis, cellulitis, myositis, septic arthritis, osteomyelitis, bovine mastitis, and canine pyoderma, all as affected by group A streptococcal bacteria.

In accordance with the invention, a preferred method of detecting the presence of Cpa1 or Cpa49 proteins involves the steps of obtaining a sample suspected of containing group A streptococci. The sample may be taken from an individual, for example, from one's blood, saliva, tissues, bone, muscle, cartilage, or skin. The cells can then be lysed, and the DNA extracted, precipitated and amplified. Detection of DNA from group A streptococci can be achieved by hybridizing the amplified DNA with a probe for GAS that selectively hybridizes with the DNA as described above. Detection of hybridization is indicative of the presence of group A streptococci.

Preferably, detection of nucleic acid (e.g. probes or primers) hybridization can be facilitated by the use of detectable moieties. For example, the probes can be labeled with biotin and used in a streptavidin-coated microtiter plate assay. Other detectable moieties include radioactive labeling, enzyme labeling, and fluorescent labeling, for example.

DNA may be detected directly or may be amplified enzymatically using polymerase chain reaction (PCR) or other amplification techniques prior to analysis. RNA or cDNA can be similarly detected. Increased or decrease expression of Cpa1 or Cpa49 can be measured using any of the methods well known in the art for the quantification of nucleic acid molecules, such as, for example, amplification, PCR, RT-PCR, RNase protection, Northern blotting, and other hybridization methods.

Diagnostic assays for Cpa1 or Cpa49 proteins or active portions thereof, such as consensus or variable sequence amino acid motifs, or anti-Cpa1 or Cpa49 antibodies may also be used to detect the presence of a streptococcal bacterium such as Streptococcus pyogenes. Assay techniques for determining protein or antibody levels in a sample are well known to those skilled in the art and include methods such as radioimmunoasssay, Western blot analysis and ELISA assays.

The isolated, recombinant or synthetic proteins of the present invention, or antigenic portions thereof (including epitope-bearing fragments), or fusion proteins including the Cpa1 or Cpa49 proteins as described above, can be administered to animals as immunogens or antigens, alone or in combination with an adjuvant, for the production of antibodies reactive with Cpa1 or Cpa49 proteins or portions thereof. In addition, the proteins can be used to screen antibodies or antisera for hyperimmune patients from whom can be derived specific antibodies having a very high affinity for the proteins.

Antibodies to Cpa1 or Cpa49, or to fragments t can also be used in accordance with the invention for the specific detection of collagen-binding streptococcal proteins, for the prevention of infection from group A streptococci, for the treatment of an ongoing infection, or for use as research tools. The term "antibodies" as used herein includes monoclonal, polygonal, chimeric, single chain, bispecific, simianized, and humanized or primatized antibodies as well as Fab fragments, including the products of an Fab immunoglobulin expression library. Generation of any of these types of antibodies or antibody fragments is well known to those skilled in the art. In the present case, specific polyclonal antiserum against Cpa has been generated which reacts with Cpa in Western immunoblots and ELISA assays and interferes with Cpa binding to collagen. The antiserum can be used for specific agglutination assays to detect bacteria which express Cpa on their surface. The antiserum does not cross-react with bacteria which express the fibronectin-binding protein F1 on their surface, although a portion of protein F1 exhibits sequence homologies to Cpa1 and Cpa49.

Any of the above described antibodies may be labeled directly with a detectable label for identification and quantification of group A streptococci. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

Alternatively, the antibody may be labeled indirectly by reaction with labeled substances that have an affinity for immunoglobulin. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Antibodies to the collagen-binding proteins Cpa1 or Cpa49, or portions thereof, may also be used in production facilities or laboratories to isolate additional quantities of the proteins, such as by affinity chromatography. For example, antibodies to the collagen-binding protein Cpa1 or Cpa49 may also be used to isolate additional amounts of collagen.

The isolated proteins of the present invention, or active fragments thereof, and antibodies to the proteins may be useful for the treatment and diagnosis of group A streptococcal bacterial infections as described above, or for the development of anti-group A streptococcal vaccines for active or passive immunization. Further, when administered as pharmaceutical composition to a wound or used to coat medical devices or polymeric biomaterials in vitro and in vivo, both the proteins and the antibodies are useful as blocking agents to prevent or inhibit the binding of group A streptococci to the wound site or the biomaterials themselves. Preferably, the antibody is modified so that it is less immunogenic in the patient to whom it is administered. For example, if the patient is a human, the antibody may be "humanized" by transplanting the complimentarity determining regions of the hybridoma-derived antibody into a human monoclonal antibody as described, e.g., by Jones et al, *Nature* 321:522–525 (1986) or Tempest et al., *Biotechnology* 9:266–273 (1991).

Medical devices or polymeric biomaterials to be coated with the antibodies, proteins and active fragments described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethra/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the protein, antibody, or active fragment to a surface of the device, preferably an outer surface that would be exposed to streptococcal bacterial infection. The surface of the device need not be entirely covered by the protein, antibody or active fragment.

In addition, the present invention may be utilized as immunological compositions, including vaccines, and other pharmaceutical compositions containing the Cpa1 or Cpa49 proteins or portions thereof are included within the scope of the present invention. Either one or both of the Cpa1 or Cpa49 proteins, or active or antigenic fragments thereof, or fusion proteins thereof, can be formulated and packaged, alone or in combination with other antigens, using methods and materials known to those skilled in the art for vaccines. The immunological response may be used therapeutically or prophylactically and may provide antibody immunity or cellular immunity, such as that produced by T lymphocytes.

The immunological compositions, such as vaccines, and other pharmaceutical compositions can be used alone or in combination with other blocking agents to protect against human and animal infections caused by or exacerbated by group A streptococci. In particular, the compositions can be used to protect humans against skin infections such as impetigo and eczema, as well as mucous membrane infections such as tonsillopharyngitis. In addition, effective amounts of the compositions of the present invention may be used to protect against complications caused by localized infections such as sinusitis, mastoiditis, parapharygeal abscesses, cellulitis, necrotizing fascitis, myositis, streptococcal toxic shock syndrome, pneumonitis endocarditis, meningitis, osteomylitis, and many other sever diseases.

Further, the present compositions can be used to protect against nonsuppurative conditions such as acute rheumatic fever, acute glomerulonephritis, obsessive/compulsive neurologic disorders and exacerbations of forms of psoriasis such as psoriasis vulgaris. The compositions may also be useful as appropriate in protecting both humans and other species of animals where needed to combat similar group A streptococcal infections.

To enhance immunogenicity, the proteins may be conjugated to a carrier molecule. Suitable immunogenic carriers include proteins, polypeptides or peptides such as albumin, hemocyanin, thyroglobulin and derivatives thereof, particularly bovine serum albumin (BSA) and keyhole limpet hemocyanin (KLH), polysaccharides, carbohydrates, polymers, and solid phases. Other protein derived or non-protein derived substances are known to those skilled in the art. An immunogenic carrier typically has a molecular weight of at least 1,000 Daltons, preferably greater than 10,000 Daltons. Carrier molecules often contain a reactive group to facilitate covalent conjugation to the hapten. The carboxylic acid group or amine group of amino acids or the sugar groups of glycoproteins are often used in this manner. Carriers lacking such groups can often be reacted with an appropriate chemical to produce them. Preferably, an immune response is produced when the immunogen is injected into animals such as mice, rabbits, rats, goats, sheep, guinea pigs, chickens, and other animals, most preferably mice and rabbits. Alternatively, a multiple antigenic peptide comprising multiple copies of the protein or polypeptide, or an antigenically or immunologically equivalent polypeptide may be sufficiently antigenic to improve immunogenicity without the use of a carrier.

The Cpa1 or Cpa49 proteins or portions thereof, or combination of proteins, may be administered with an adjuvant in an amount effective to enhance the immunogenic response against the conjugate. At this time, the only adjuvant widely used in humans has been alum (aluminium phosphate or aluminum hydroxide). Saponin and its purified component Quil A, Freund's complete adjuvant and other adjuvants used in research and veterinary applications have toxicities which limit their potential use in human vaccines. However, chemically defined preparations such as muramyl dipeptide, monophosphoryl lipid A, phospholipid conjugates such as those described by Goodman-Snitkoff et al. *J. Immunol.* 147:410–415 (1991) and Incorporated by reference herein, encapsulation of the conjugate within a proteoliposome as described by Miller et al., *J. Exp. Mod.* 176: 1739–1744 (1992) and incorporated by reference herein, and encapsulation of the protein in lipid vesicles such as Novasome™ lipid vesicles (Micro Vescular Systems, Inc., Nashua, N.H.) may also be useful.

The term "vaccine" as used herein includes DNA vaccines in which the nucleic acid molecule encoding for a collagen-binding Gas protein, such as the nucleic acid sequences disclosed herein as SEQ ID NOS. 1 or 3, as used in a pharmaceutical composition is administered to a patient. For genetic immunization, suitable delivery methods known to those skilled in the art include direct injection of plasmid DNA into muscles (Wolff et al., *Hum. M. Genet.* 1:363, 1992), delivery of DNA completed with specific protein carriers (Wu et al., *J. Biol. Chem.* 264:16985, 1989), coprecipitation of DNA with calcium phosphate (Benvenisty and Reshef, *Proc. Natl. Acad. Sci.* 83:9551, 1986), encapsulation of DNA in liposomes (Kaneda et al., *Science* 243:375, 1989), particle bombardment (Tang et al., *Nature* 356:152, 1992 and Eisenbraun et al., *DNA Cell Biol.* 12:791, 1993), and in vivo infection using cloned retroviral vectors (Seeger et al., *Proc. Natl. Acad. Sci.* 81:5849, 1984).

In another embodiment, the invention is a polynucleotide which comprises contiguous nucleic acid sequences capable of being expressed to produce a gene product upon introduction of said polynucleotide into eukaryotic tissues in vivo. The encoded gene product preferably either acts as an immunostimulant or as an antigen capable of generating an immune response. Thus, the nucleic acid sequences in this embodiment encode an immunogenic epitope, and optionally a cytokine or a T-cell costimulatory element, such as a member of the B7 family of proteins.

There are several advantages of immunization with a gene rather than its gene product. The first is the relative simplicity with which native or nearly native antigen can be presented to the immune system. Mammalian proteins expressed recombinantly in bacteria, yeast, or even mammalian cells often require extensive treatment to ensure appropriate antigenicity. A second advantage of DNA immunization is the potential for the immunogen to enter the MHC class I pathway and evoke a cytotoxic T cell response. Immunization of mice with DNA encoding the influenza A nucleoprotein (NP) elicited a $CD8^+$ response to NP that protected mice against challenge with heterologous strains of flu. (See Montgomery, D. L. et al., *Cell Mol Biol*, 43(3):285–92, 1997 and Ulmer, J. et al., *Vaccine*, 15(8): 792–794, 1997.)

Cell mediated immunity is important in controlling infection. Since DNA immunization can evoke both humoral and cell-mediated immune responses, its greatest advantage may be that it provides a relatively simple method to survey a large number of *S. pyogenes* genes for their vaccine potential.

Pharmaceutical compositions containing the Cpa1 or Cpa49 proteins or portions thereof, nucleic acid molecules, antibodies, or fragments thereof, may be formulated in combination with a pharmaceutical excipient or carrier such as saline, dextrose, water, glycerol, ethanol, other therapeutic compounds, and combinations thereof. The formulation should be appropriate for the mode of administration. The compositions are useful for interfering with, modulating, or inhibiting binding interactions between streptococcal bacteria and collagen on host cells.

The amount of expressible DNA or transcribed RNA to be introduced into a vaccine recipient will have a very broad dosage range and may depend on the strength of the transcriptional and translational promoters used. In addition, the magnitude of the immune response may depend on the level of protein expression and on the immunogenicity of the expressed gene product. In general, effective dose ranges of about 1 ng to 5 mg, 100 ng to 2.5 mg, 1 μg to 750 μg, and preferably about 10 μg to 300 μg of DNA is administered directly into muscle tissue. Subcutaneous injection, intradermal introduction, impression through the skin, and other modes of administration such as intraperitoneal, intravenous, or inhalation delivery are also suitable. It is also contemplated that booster vaccinations may be provided. Following vaccination with a polynucleotide immunogen, boosting with protein immunogens such as the Cpa1 or Cpa49 gene product is also contemplated.

The polynucleotide may be "naked", that is, unassociated with any proteins, adjuvants or other agents which affect the recipient's immune system. In this case, it is desirable for the polynucleotide to be in a physiologically acceptable solution, such as, but not limited to, sterile saline or sterile buffered saline. Alternatively, the DNA may be associated with liposomes, such as lecithin liposomes or other liposomes known in the art, as a DNA-liposome mixture, or the DNA may be associated with an adjuvant known in the art to boost immune responses, such as a protein or other carrier. Agents which assist in the cellular uptake of DNA, such as, but not limited to, calcium ions, may also be used. These agents are generally referred to herein as transfection facilitating reagents and pharmaceutically acceptable carriers. Techniques for coating microprojectiles coated with polynucleotide are known in the art and are also useful in connection with this invention. For DNA intended for human use it may be useful to have the final DNA product in a pharmaceutically acceptable carrier or buffer solution. Pharmaceutically acceptable carriers or buffer solutions are known in the art and include those described in a variety of texts such as Remington's Pharmaceutical Sciences.

It is recognized by those skilled in the art that an optimal dosing schedule for a DNA vaccination regimen may include as many as five to six, but preferably three to five, or even more preferably one to three administrations of the immunizing entity given at intervals of as few as two to four weeks, to as long as five to ten years, or occasionally at even longer intervals.

Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

In a preferred embodiment, a vaccine is packaged in a single dosage for immunization by parenteral (i.e., intramuscular, intradermal or subcutaneous) administration or nasopharyngeal (i.e., intranasal) administration. The vaccine is most preferably injected intramuscularly into the deltoid muscle. The vaccine is preferably combined with a pharmaceutically acceptable carrier to facilitate administration. The carrier is usually water or a buffered saline, with or without a preservative. The vaccine may be lyophilized for resuspension at the time of administration or in solution.

Microencapsulation of the protein will give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters, polyamides, poly (D,L-lactide-co-glycolide) (PLGA) and other biodegradable polymers. The use of PLGA for the controlled release of antigen is reviewed by Eldridge et al., CURRENT TOPICS IN MICROBIOLOGY AND IMMUNOLOGY, 146:59–66 (1989).

The preferred dose for human administration is from 0.01 mg/kg to 10 mg/kg, preferably approximately 1 mg/kg. Based on this range, equivalent dosages for heavier body weights can be determined. The dose should be adjusted to suit the individual to whom the composition is administered and will vary with age, weight and metabolism of the individual. The vaccine may additionally contain stabilizers or pharmaceutically acceptable preservatives, such as thimerosal (ethyl(2-mercaptobenzoate-S)mercury sodium salt) (Sigma Chemical Company, St. Louis, Mo.).

When labeled with a detectable biomolecule or chemical, the collagen-binding proteins described herein are useful for purposes such as in vivo and in vitro diagnosis of streptococcal infections or detection of group A streptococcal bacteria. Laboratory research may also be facilitated through use of such protein-label conjugates. Various types of labels and methods of conjugating the labels to the proteins are well known to those skilled in the art. Several specific labels are set forth below. The labels are particularly useful when conjugated to a protein such as an antibody or receptor. For example, the protein can be conjugated to a radiolabel such as, but not restricted to, $^{32}$P, $^{3}$H, $^{14}$C, $^{35}$S, $^{125}$I, or $^{131}$I. Detection of a label can be by methods such as scintillation counting, gamma ray spectrometry or autoradiography.

Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light. Fluorogens may also be used to label proteins. Examples of fluorogens include fluorescein and derivatives, phycoerythrin, allophycocyanin, phycocyanin, rhodamine, and Texas Red. The fluorogens are generally detected by a fluorescence detector.

The protein can alternatively be labeled with a chromogen to provide an enzyme or affinity label. For example, the protein can be biotinylated so that it can be utilized in a biotin-avidin reaction, which may also be coupled to a label such as an enzyme or fluorogen. For example, the protein can be labeled with peroxidase, alkaline phosphatase or other enzymes giving a chromogenic or fluorogenic reaction upon addition of substrate. Additives such as 5-amino-2,3-dihydro-1,4-phthalazinedione (also known as Luminol$^a$) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used. Such labels can be detected using enzyme-linked immunoassays (ELISA) or by detecting a color change with the aid of a spectrophotometer. In addition, proteins may be labeled with colloidal gold for use in immunoelectron microscopy in accordance with methods well known to those skilled in the art.

The location of a ligand in cells can be determined by labeling an antibody as described above and detecting the label in accordance with methods well known to those skilled in the art, such as immunofluorescence microscopy using procedures such as those described by Warren and Nelson (*Mol. Cell. Biol.,* 7: 1326–1337, 1987).

In addition to the therapeutic compositions and methods described above, the Cpa1 and Cpa49 proteins or active portions or fragments thereof, nucleic acid molecules or antibodies are useful for interfering with the initial physical interaction between a pathogen and mammalian host responsible for infection, such as the adhesion of bacteria, to mammalian extracellular matrix proteins such as collagen on in-dwelling devices or to extracellular matrix proteins in wounds; to block Cpa1 or Cpa49 protein-mediated mammalian cell invasion; to block bacterial adhesion between collagen and bacterial Cpa1 or Cpa49 proteins or portions thereof that mediate tissue damage; and, to block the normal progression of pathogenesis in infections initiated other than by the implantation of in-dwelling devices or surgical techniques.

The Cpa1 or Cpa49 proteins, or active fragments thereof, are useful in a method for screening compounds to identify compounds that inhibit collagen binding of streptococci to host molecules. In accordance with the method, the compound of interest is combined with one or more of the Cpa1 or Cpa49 proteins or fragments thereof and the degree of binding of the protein to collagen or other extracellular matrix proteins is measured or observed. If the presence of the compound results in the inhibition of protein-collagen binding, for example, then the compound may be useful for inhibiting group A streptococci in vivo or in vitro. The method could similarly be used to identify compounds that promote interactions of GAS with host molecules. The method is particularly useful for identifying compounds having bacteriostatic or bacteriocidal properties.

For example, to screen for GAS agonists or antagonists, a synthetic reaction mixture, a cellular compartment (such as a membrane, cell envelope or cell wall) containing one or more of the Cpa1 or Cpa49 proteins or fragments thereof and a labeled substrate or ligand of the protein is incubated in the absence or the presence of a compound under investigation. The ability of the compound to agonize or antagonize the protein is shown by a decrease in the binding of the labeled ligand or decreased production of substrate product. Compounds that bind well and increase the rate of product formation from substrate are agonists. Detection of the rate or level of production of product from substrate may be enhanced by use of a reporter system, such as a calorimetric labeled substrate converted to product, a reporter gene that is responsive to changes in Cpa1 or Cpa49 nucleic add or protein activity, and binding assays known to those skilled in the art. Competitive inhibition assays can also be used.

Potential antagonists include small organic molecules, peptides, polypeptides and antibodies that bind to Cpa1 or Cpa49 nucleic acid molecules or proteins or portions thereof and thereby inhibit their activity or bind to a binding molecule (such as collagen to prevent the binding of the Cpa1 or Cpa49 nucleic acid molecules or proteins to its ligand. For example, a compound that inhibits Cpa1 or Cpa49 activity may be a small molecule that binds to and occupies the binding site of the Cpa1 or Cpa49 protein, thereby preventing binding to cellular binding molecules, to prevent normal biological activity. Examples of small molecules include, but are not limited to, small organic molecule, peptides or peptide-like molecules. Other potential antagonists include antisense molecules. Preferred antagonists include compounds related to and variants or deriva tives of the Cpa1 or Cpa49 proteins or portions thereof. The nucleic acid molecules described herein may also be used to screen compounds for antibacterial activity.

The invention further contemplates a kit containing one or more Cpa1 or Cpa49-specific nucleic acid probes, which can be used for the detection of collagen-binding proteins from group A streptococci in a sample, or for the diagnosis of GAS bacterial infections. Such a kit can also contain the appropriate reagents for hybridizing the probe to the sample and detecting bound probe. In an alternative embodiment, the kit contains antibodies specific to either or both Cpa1 and Cpa49 proteins or active portions thereof which can be used for the detection of group A streptococci.

In yet another embodiment, the kit contains either or both the Cpa1 and Cpa49 proteins, or active fragments thee, which can be used for the detection of GAS bacteria or for the presence of antibodies to collagen-binding GAS proteins in a sample. The kits described herein may additionally contain equipment for safely obtaining the sample, a vessel for containing the reagents, a timing means, a buffer for diluting the sample, and a colorimeter, reflectometer, or standard against which a color change may be measured.

In a preferred embodiment, the reagents, including the protein or antibody, are lyophilized, most preferably in a single vessel. Addition of aqueous sample to the vessel results in solubilization of the lyophilized reagents, causing them to react. Most preferably, the reagents are sequentially lyophilized in a single container, in accordance with methods well known to those skilled in the art that minimize reaction by the reagents prior to addition of the sample.

TABLE 1

Sequence homologies of the ORFs of the GAS nra genomic region

| GAS ORF (provisional) number/designation | Homologous protein sequence; source organism | Percentage identity/similarity | Reference |
|---|---|---|---|
| 1 (msmRL) | Multiple sugar metabolism regulator; *Streptococcus mutans* | 34/59 | Russell et al. (1992) |
| 2 (ORF2) | Bo homologous sequence identified | — | — |
| 3 (etfLSL) | C-terminus of electron transfer flavoprotein 1a; *Methylophilus methylptrophus* | 27/47 | Chen and Swenson (1994) |
| 4 (lepAL) | Signal peptidase t; *Staphylococcus aureus* | 46/67 | Cregg et al (1996) |
| cpa | Protein F; *Streptococcus pyogenes* | 28/41 | Hanski and Caparon (1992) |
| nra | RofA regulator of protein F; *Streptococcus pyogenes* | 63/73 | Fogg et al. (1994) |
| 5 (ORF5) | Hypothetical 31.8 kDa protein in ftsH-cysK intergenic region; *Bacillus subtilis* | 35/62 | Ogasawara et al. (1994) |
| 6 (nifR3L) | Nitrogenase regulator; *Azospirillum brasilense* | 32/46 | Machado et al. (1995) |
| | Hypothetical 37.1 kDa protein; *Bacillus subtilis* | 59/75 | Ogasawara et al. (1994) |
| 7 (kinL) | dA/dG-kinase; *Lactobacillus acidophilus* | 57/74 | Ma et al. (1995) |
| 8 (ssbL) | Single-strand DNA-binding protein; *Bacillus subtilis* | 50/65 | Rikke et al. (1995) |
| 9 (phc7L) | Phenylalanyl-tRNA synthase beta subunit; *Bacillus subtilis* | 49/62 | Brakhage et al. (1990) |

TABLE 2

Presence of nral rofA(-associated) genes in selected GAS serotype strains.

| Serotype strain | Regulatory genes | | Structurel genes | | |
|---|---|---|---|---|---|
| | nra | rofA | prtF | prtF2 | cpa |
| M1 | − | + | − | − | + |
| M2 | − | + | − | − | − |
| M3 | + | + | + | − | − |
| M4 | + | + | − | + | − |
| M5 | + | + | − | + | − |
| M6 | − | + | + | − | − |
| M12 | − | + | + | + | − |
| M18 | + | + | − | + | − |
| M24 | − | + | + | − | − |
| M49 | + | − | − | + | + |

Genes were detected with specific probes used for genomic Southern blot hybridizations as well as by specific PCR assays. Sequences of primers used for analytical PCRs or to generate probes are Shown in Table 4.
+.hybridizataon/PCR product detectable:
−.no hybridization/PCR product detectable.

TABLE 3

Human matrix protein-binding activity of a recombinant Cpa protein.

|  | Collagen | Fibronectin | Laminin | BSA |
|---|---|---|---|---|
| Cpa/Maf fusion | 0.373 ± 0.011 | 0.074 ± 0.006 | 0.115 ± 0.036 | 0.049 ± 0.021 |
| Mal | 0.104 ± 0.007 | 0.042 ± 0.002 | 0.060 ± 0.006 | 0.033 ± 0.005 |
| HRPO (negative control) | 0.049 ± 0.013 | 0.038 ± 0.015 | 0.038 ± 0.012 | 0.028 ± 0.006 |

The binding activity of a purified Cpa-maltose binding protein fusion and the maltose-binding protein alone (Mal), both coupled to horseradish peroxidase (HRPO), were compared with that of HRPO alone. The assay was performed in an ELISA format as described in Experimental procedures. The results were read as $OD_{492}$ values. The data were analysed by the Wilcoxon range test and the binding of the Cpa-Mal fusion to collagen type I and to laminin was found to be statistically significant ($P < 0.05$).

TABLE 4

List of oligonucleotides used in this work.

| Designation | Sequence (5' to 3') | Sequence ID. No. | Position Numbers | Reference |
|---|---|---|---|---|
| A. | | | | |
| nra FOR | ATTTTTTCTCATGTTGCTA | SEQ ID NO:6 | 6474-6492 | This study |
| nra REV | GTTTAGAATGGTTTAATTG | SEQ ID NO:7 | 7308-7290 | This study |
| rofA FOR | GCCAATAACTGAGGTAGC | SEQ ID NO:8 | 141-158 | Fogg et al. (1994) |
| rofA REV | GGCTTTTGCTCTTTTAGGT | SEQ ID NO:9 | 995-977 | Fogg et al. (1994) |
| cpa FOR | AGTTCACAAGTTGTCTACTG | SEQ ID NO:10 | 3435-3454 | This study |
| cpa REV | AAATAATAGATAGCAAGCTG | SEQ ID NO:11 | 3727-3708 | This study |
| prtF FOR | ATTAATGCCAGAGTTAGATG | SEQ ID NO:12 | 1414-1433 | Hanski and Caparon (1992) |
| prtF REV | CGATTCTCTTCCACTTTG | SEQ ID NO:13 | 2259-2242 | Hanski and Caparon (1992) |
| prtF2 FOR | TACTCTGTTAAAGAAGTAACTG | SEQ ID NO:14 | 2260-2281 | Jaffe et al. (1996) |
| prtF2 REV | CTCAGAGTCACTTTCTGG | SEQ ID NO:15 | 3168-3151 | Jaffe et al. (1996) |
| nifR3 FOR | GGATTTTGCCTACTACTTA | SEQ ID NO:16 | 8443-8461 | This study |
| nifR3 REV | GTGGAATATCTAAAACAGAC | SEQ ID NO:17 | 9313-9294 | This study |
| B. | | | | |
| nra-ins FOR | TTTTATTGGAGACTAGAAGTTTA | SEQ ID NO:18 | 6325-6347 | This study |
| nra-ins REV | AGCAAGCCACTGATTTAC | SEQ ID NO:19 | 7481-7464 | This study |
| cpa-ins FOR | TGCAAAAGAGGGATAAAAC | SEQ ID NO:20 | 5932-5914 | This study |
| cpa-ins REV | GAAGCAGTAGACAACTTGTG | SEQ ID NO:21 | 4707-4726 | This study |
| nraLuc FOR1 | TAAACTAAAGTAGCTTAGCA | SEQ ID NO:22 | 5953-5972 | This study |
| nraLuc FOR5 | ATGGAACGTCATCACAAC | SEQ ID NO:23 | 6688-6705 | This study |
| nraLuc REV1 | CAGATACCTAAAAATAAACG | SEQ ID NO:24 | 7930-7911 | This study |
| cpa-pMAL FOR | GCTGAAGAACAATCAGTACCA | SEQ ID NO:25 | 5798-5778 | This study |
| cpa-pMAL REV | TTAGTCATTTTTTAACCCTTTACG | SEQ ID NO:26 | 3705-3728 | This study |
| C. | | | | |
| RT-nra FOR | CTTTTTACTTATTAAGAGATGA | SEQ ID NO:27 | 7669-7690 | This study |
| RT-nra REV | CTCGTTTAGAAAATCTTG | SEQ ID NO:28 | 7886-7869 | This study |

TABLE 4-continued

List of oligonucleotides used in this work.

| Designation | Sequence (5' to 3') | Sequence ID. No. | Position Numbers | Reference |
|---|---|---|---|---|
| RT-orf5 FOR | AAAATAATTAAATCAATAGCA | SEQ ID NO:29 | 8030-8050 | This study |
| RT-orf5 REV | CCACAGAGATAATGTGT | SEQ ID NO:30 | 8258-8241 | This study |

Oligonucleotides were used as primers to PCR amplify probes for Southern and Northern blot hybridizations (A), genomic Fragments for cloning into pFW11, pFW11-luc or pMAL-c2 plasmids (B) and primers for RT-PCR to detect nra and orf5-specific transcripts (C). Primer pairs nra-ins FOR/REV, cpa-ins FOR/REV, nraLuc FOR/REV and cpa-pMAL FOR/REV were 5' extended with SphI/SpeI. NheI/BamHI and BAMHI/PstI sites, respectively, to facilitate forced cloning of the resulting PCR products. The nucleotide position numbers refer to the GAS nra genomic sequence as submitted to Genbank or the cited publications.

EXAMPLES

The following examples are provided which exemplify aspects of the preferred embodiments of the present invention. It should be appreciated by those of skill in the art that the techniques disclosed in the examples which follow represent techniques discovered by the inventors to function well in the practice of the invention, and thus can be considered to constitute pupated modes for its practice. However, those of skill in the art should, in light of the present disclosure, appreciate that many changes can be made in the specific embodiments which are disclosed and still obtain a like or similar result without departing from the spirit and scope of the invention.

Example 1

Isolation of Group A Streptococcal Proteins

A. Bacterial Strains and Culture Conditions

GAS serotype M49 strain CS101 was provided by P. Cleary, MN, USA Serotypes M1, M2, M3, M4, M5, M6, M12, M18 and M24 GAS strains T1/195/2, T2/44/RB4.119, B930/60/2, 75-194, T5B/126/3, S43/192/1, T12/126/4, J17C/55/1 and 71-694 were obtained from D. Johnson, MN, USA The M49 GAS isolates B737/137/1, 49-49/123, 88-299, 90-053, 90-397, 89-288, 90-306 and 8314/1945 have been described by Kaufhold et al. (1992). E coli strain Blue MRF served as a host for phage Lambda ZAP Express. E. coli stain DH5a was used as host for plasmids pFW11 and pMAL-c2.

E. coli DH5a isolates transformed with pFW11 or pMAL-c2 derivatives were grown on disk sensitivity testing agar (Unipath) supplemented with 100 mgl$^{-1}$ spectinomyccin or 50 mgl$^{-1}$ ampicillin respectively. E coli Blue MRF strains infected with recombinant lambda phases were grown in NZ casamino acids/yeast extract (NZY) agar according to the instructions of the supplier (Stratagene). All E coli cultures were grown in cultures were grown at 37° C. in ambient air.

GAS strains were cultured in TH broth and on TH agar (Unipath) both supplemented with 0.5% yeast exact (THY), or in chemically defined medium (CDM) (van de Rijn and Kessler, 1980). The GAS mutant strains were maintained in medium containing 60 mgl$^{-1}$ spectinomycin. Culture conditions for GAS strains were a temperature of 37° C. and a 5% $CO_2$/20% $O_2$ atmosphere unless specifically described.

B. Vectors

E coli phage Lambda ZAP Express (BamHI arms, CIP treated) was purchased from Stratagene and used according to the instructions of the manufacturer.

Plasmid pFW11 was used for insertional mutagenesis as described by Podbielski et at. (1996c). Plasmid pFW11 multiple cloning site (MCS) 1. The luciferase (luc) box was amplified by PCR using plasmid pUSL2/5 (Gräfe et at., 1996) as template and oligonucleotides lucFor (5'GAC-GATCTCGAGGAGGTAAATGAAGACGCCAAAAAC-3') (SEQ ID NO:31) lucRev (5'GACGATAAGCTTTTA-CAATTTGGACTTTCCG-3') (SEQ ID NO:32) as primers. The luciferase box contained an optimized Shine-Dalgarno sequence as well as the luc start and stop codons. Cloning of GAS genomic fragments into MCS1 of pFW11-luc followed the protocol outlined by Podbielski et at. (1996c).

Plasmid pMAL-c2 was used for expression of the cpa gene and was purchased from New England Biolabs. It was used according to the instructions of the manufacturer.

C. DNA Techniques

Chromosomal GAS DNA was prepared by the method of Martin et al. (1990). Plasmid DNA preparations and genetic manipulations as well as other conventional DNA techniques were performed as described by Ausabel et al., (1990). Transformation of GAS strains by electroporation was according to the protocol of Caparon and Scott (1991).

Usage of the serotype M49 GAS Lambda library for sequencing of recombinant GAS genomic DNA followed the protocol of Podbielski et al., (1996b). Oligonucleotides used for sequencing and PCR were designed with the aid of OLIGO 5.0 (National Biosciences), synthesized on an OLIGO 1000 DNA synthesizer (Beckman) and desalted through NAP5 columns (Pharmacia). The parameters of PCR assays, direct labeling of PCR products with DIG-dUTP, analysis of PCR products and parameters for direct sequencing of PCR products were as described previously (Podbielski et al., 1995).

DNA sequences were compiled and analyzed with PC GENE 6.8 (IntelliGenetics). Sequence comparisons were performed using the BLAST programs and the databases of the GenBank data library as well as the Streptococcal Genome Sequencing Project of the University of Oklahoma, USA (Roe et al., 1997).

D. RNA Preparation and Analysis

For RNA preparations, serotype M49 GAS strains were grown aerobically to $OD_{600}$ values of 0.2, 0.5, and 0.9, which correspond to early, medium and late logarithmic growth phases respectively. Before preparation, cells were sedimented by 2 min centrifugation at 4° C., suspending in ice-cold 20 mM Tris (pH 7.5)/5 mM $MgCl_2$/20 mM sodium azide/400 mgl$^{-1}$ chloramphenicol. RNA preparation followed the protocol of Shaw and Clewell (1985). Denaturing agarose gel electrophoresis and Northern blot hybridizations with DIG-dUTP-labeled probes were performed as described previously (Pidbielski et al., 1995). Probes were generated by asymmetric PCR, using only $10^{-2}$ to $10^{-3}$ of the normal amounts of the appropriate upstream primers.

RT-PCR was performed with RNA after 30 min exposure to DNase I according to the manufacturer's protocol (Boehringer Mannheim). Reverse transcription using SuperScript II RT-polymerase was done as described by the manufacturer (Gibco BRL) using the appropriate downstream primers (Table 4). One microlite of the RT assay was used as template for PCR employing the PCR primers listed in Table 4. Controls included primer control with genomic DNA template, reagent contamination control by running both reactions without RNA template, and DNA contamination control by running both reaction without RT-polymerase.

E. DNA Mutagenesis Experiments

Insertional inactivation of the nra gene was performed using a recombinant pFW11 plasmid following the strategy and specific methods according to Podbielski et al. (1996c). The primers nra-insFOR/REV and cpa insFOR/REV annealing to nra and cpa internal sequences were used to generate PCR products, which were cloned into pFW11 via the SphI/SpeI or NheI/BamHI sites of MCS1. Specific integration of the nra recombinant plasmid into the GAS genome was confirmed by Southern blot hybridization using BamHI-, SpeI- and XbaI-digested genomic DNA and probes specific for the integrated antibiotic resistance marker aad9 as well as for the duplicated nra sequence.

Construction of the nra promoter-luciferase fusions was performed using plasmid pFW11-luc (this study) and PCR products comprising the 3' end of the nra gene or the entire nra promoter and structural gone region. For amplification of the PCR product, primers nraLucFOR5 or nraLucFOR1, and nraLucREV1 were used (Table 4). The primers annealed in the central region of the nra gene or immediately upstream of the cps gene (FIG. 1) and at the stop codon of the nra gene. Using NheI and BamHI sites as 5' tags for the upstream and downstream primers, respectively, the resulting PCR products were cloned into the corresponding MCS1 site of pFW11-luc. Specific integration of the plasmid in the GAS genome was confirmed as shown.

F. Measuring Adherence to Immobilized Human Matrix Proteins

Cells grown on solid medium were prepared by spreading a 10 µl aliquot of oversight cultures onto fresh THY agar plates and incubating the plates overnight in ambient air, 5% $CO_2$ or anerobic incubators. Plates were then flooded with 3 ml of DPBS, pH 7.4 (PBS plus 0.88 mM $CaCl_2$/0.45 mM $MgCl_2$) and incubated for 10 min at room temperature. Cells were suspended gently using a glass spreader, removed from the plate with a pipette avoiding the production of air bubbles and transferred into a test tube. Cells were then suspended by gentle, repeated pipetting.

Labeling of bacteria and adhesion assays followed a protocol of Geelen et al., (1993). Specifically, for labeling of bacteria, thoroughly suspended cells were washed in 12 ml of DPBS and suspended in 2 ml of FITC solution (1 mg ml$^{-1}$ FITC in 50 mM sodium carbonate buffer, pH 9.2, stored in the dark and passed through a 0.2 µm pore size filter before use). After 20 min incubation at room temperature in the dark, cells were sedimented by Nation, washed in DPBS, suspended in 2 ml of DPBS and sonicated for 20 s at setting 4 in the refrigerated hollow horn of the sonifier 450 (Branson Ultrasonic). The $OD_{600}$ values of the suspension were adjusted to 1.0 with DPBS, sonicated again to disruption of aggregates and kept in the dark until used.

For immobilization of human matrix proteins, Terasaki microtitre plates were washed once with DPBS, pH 7.4. Then, 10 ml of 100 µg ml$^{-1}$ human fibronectin or collagen type 1 (Gibco BRL) was added to the wells and incubated overnight at room temperature in a moist chamber.

The preincubated Terasaki microtitre plates were washed with DPBS, and residual buffer was carefully removed. Then, 10 µl aliquots of FITC-labeled cell suspensions were added to the wells and incubated for 60 min at 37° C. in a 5% $CO_2$/20% $O_2$ atmosphere. The plates were then washed five times with DPBS, and bound cells were fixed by flooding plates with 0.5% glutaraldehyde for 5 min. The plates were again washed twice with DPBS and kept in the dark until measured. The intensity of FITC labeling was controlled for each assay by measuring the fluorescence intensity of 10 µl aliquots of cells added in triplicate to uncoated DPBS-washed Terasaki microtitre plates and directly counted.

Fluorescence of single wells was evaluated by processing the plates through an automated Cyto Fluor II fluorescene reader (PerSeptive Biosystems) operating with excitation and detection wavelengths of 485 nm and 530 nm respectively. Sensitivity gain levels of 72 or 62 were used for binding assays and FITC-labeling control respectively.

For each assay, adherence to a human protein was measured for at least two coated plates and four replicate wells each located at different positions on the plates. For both matrix proteins, the assays were repeated at least four times on different days. To normalize the data, the following calculations were carried out.

The four duplicates on a given plate were averaged to give a single value ("ave-RLU'). The ave-RLU values from the nra mutants on each plate were corrected for differences in FITC labeling intensity as follows: ave-RLU×[(wild-type strain intensity of labeling)/(mutant strain intensity of labeling)].

The maximum difference for intensity of labeling was less than a factor of 2. Standardization across experiments was accomplished by multiplying all values by a standardization factor. This standardization factor was derived by comparing all subsequent experiments to the first experiment using the following scheme:

(wild-type strain intensity of labeling in assay no. 1)/(wild-type strain intensity of labeling in assay no. Y).

Once calculated, all values derived in experiment Y were multiplied by the standardization factor.

For comparison, unlabeled bacteria were tested for adherence to collagen type I and detected by a rabbit polyclonal anti-group A carbohydroxide antiserum as described by Gubbe (1997).

Example 2

Expression of a Recombinant CPA Protein and Determination of its Matrix Protein-binding Properties The entire cpa gene except for its leader peptide encoding portion was amplified by PCR using the primers cpa-pMAL FOR and cpa-pMAL REV (Table 4). The resulting product was cloned into the BamHI and Pst1 sites of plasmid pMAL-c2. Expression in the presence of 2 mM IPTG with an induction period of 4 h and subsequent non-denaturing preparation followed a protocol of Ausubel et al. (1990). Purification of the recombinant CPA-maltose binding fusion protein using a composite amylose/agarose matrix perform according to the instructions of the manufacturer (New England Biolabs). The purified fusion protein was then labeled with peroxidase as described by Schmidt et al. (1993).

Microtitre plates (96-well, flat-bottom; Nunc) were coated with BSA and human fibronectin, type I collagen or laminin (Gibco BRL) by adding 2 μg of each protein dissolved in 200 μl of 50 mM sodium carbonate, pH 8.6, to single wells. The wells were washed with PBS, pH 7.8, plus 0.5%. Tween 20 and blocked with 0.01% Tween 20 (PBS-T).

Peroxidase-labeled Cpa-maltose binding protein fusion and recombinant purified maltose-binding protein (for control of specific binding of the bacteria) were added to the wells for 2 h at room temperature. Non-conjugated peroxidase at a 1:300 dilution in PBS-T was used as a negative control. After washing with PBS-T, all wells were incubated with ortho-phenylenediamine (Sigma) and measured in an ELISA reader (SLT RainBou) set at 492 nm detection wavelength as outlined by Tijssen (1985). All assays were repeated on at least three independent occasions.

REFERENCES

Ausubel, F. M., et al. (1990) *Current Protocols in Molecular Biology*. New York.
Brakhage, A. A., et al. (1990) *Biochimie* 72: 725–734.
Caparon, M. G., and Scott, J. R. (1991) *Methods Enzymol* 204: 556–586.
Caparon, M. G., et al. (1992) *J. Bacteriol* 174: 5693–5701.
Chen, D., and Swenson, R. P. (1994) *J Biol Chen* 269: 32120–32130.
Chen, C., et al. (1993) *Mol Gen Genet* 241: 685–693.
Crater, D. L., and van de Rijn, I. (1995) *J Biol Chem* 270: 18452–18458.
Cregg, K. M., et al. (1996) *J Bacteriol* 178: 5712–5718.
Fogg, G. C., and Caparon, M. G. (1997) *J Bacteriol* 179: 6172–6180.
Fogg, G. C., et al.(1994) *Mol Microbiol* 11: 671–684.
Geelen, S., et al. (1993) *Infect Immun* 61: 1538–1543.
Gibson, C. M., and Caparon, M. (1996) *J Bacteriol* 178: 4688–4695.
Grafe, S., et al. (1996) *Med Microbiol Immunol* 185: 11–17.
Gubbe, K. (1997) PhD Thesis, Friedrich -Shiller-Universitat, Jena.
Hanski, E., and Caparon, M. (1992) *Proc Natl Acad Sci USA* 89: 6172–6176.
Hanski, E., et al. (1992) *Infect Immun* 60: 5119–5125.
Jaffe, J., et al. (1996) *Mol Microbiol* 21: 373–384.
Jenkinson, H. F., and Demuth, D. R. (1997) *Mol Microbiol* 23: 183–190.
Kaufhold, A., et al. (1992) *J Clin Microbiol* 30: 2391–2397.
Kleerebezern, M., et al. (1997) *Mol Microbiol* 24:895–904.
La Penta, D., et al. (1994) *Mol Microbiol* 12: 873–879.
McIver, K., and Scoff, J. R. (1997) *J Bacteriol* 179: 5178–5187.
McIver, KS., et al. (1995) *Infect Immun* 63: 4540–4542.
Ma, G. T., et al. (1995) *J Biol Chem* 270: 6595–6601.
Machado, H. B., et al. (1995) *Can J Microbiol* 41: 674–684.
Martin, N. J., et al. (1990) *J Clin Microbiol* 28: 1881–1886.
Natanson, S., et al. (1995) *J Infect Dis* 171: 871–878.
Ogasawara, N., et al. (1994) *DNA Res* 1: 1–14.
Okada, N., et al. (1993) *Mol Microbiol* 7: 893–903.
Okada, N., Pentland, A. P., Falk, P., and Caparon, M. G. (1994) M protein and protein F act as important determinants of cell-specific tropism of *Streptococcus pyogenes* in skin tissue. J. Clin Invest 94: 965–977.
Okada, N., et al. (1995) *Proc Natl Acad Sci USA* 92: 2489–2493.
Ozeri, V., et al. (1996) *EMBO J.* 15: 989–998.
Perez-Casal, J., et al. *J Bacteriol* 173: 2617–2624.
Podbielski, A., and Leonard, B. A. B. (1998) *Mol Microbiol* 28: 1323–1334.
Podbielski, A., et al. (1992) *Mol Microbiol* 6: 2253–2265.
Podbielski, A., et al. (1995) *Infect Immun* 63: 9–20.
Podbielski, A., et al. (1996a) *Med Microbiol Immunol* 185: 171–181.
Podbielski, A., et al. (1996b) *Mol Microbiol* 21: 1087–1099.
Podbielski, A., et al. (1996c) *Gene* 177: 137–147.
Prag, G., et al. (1997) *Mol Microbiol* 26: 619–620.
van de Rijn, I., and Kessler, R. E. (1980) *Infect Immun* 27: 444–448.
Rikke, B. A., et al. (1995) *Biochem Biophys Acta* 1261: 143–146.
Roe, B. A., et al. (1997) Streptoccocal Genome Sequencing Project. Oklahoma City: University of Oklahoma.
Russell, R. R. B., et al. (1992) *J Biol Chem* 287: 4631–4637.
Schmidt, K. H., et al. (1993) *FEMS Immunol Med Microbiol* 7: 135–144.
Sela, S., et al. (1993) *Mol Microbiol* 10: 1049–1055.
Shaw, J. H., and Clewell, D. C. (1985) *J Bacteriol* 164: 782–796.
Takahashi, I., et al. (1993) *J Bacteriol* 175: 4345–4353.
Talay, S. R., et al. (1992) *Infect Immun* 60: 3837–3844.
Talay, S. R., et al (1994) *Mol Microbiol* 13: 531–539.
Tijssen, P. (1995) Practice and theory of enzyme immunoassays. In Laboratory Techniques in Biochemistry and Molecular Biology. Amsterdam.
Van Heyningen, T., et al. (1993) *Mol Microbiol* 9: 1213–1222.
Xu, S., and Collins, C. M. (1996) *Infect Immun* 64: 5399–5402

What is claimed is:

1. An antibody or antiserum raised against an isolated collagen-binging protein from group A streptococci selected from the group consisting of Cpa1 and Cpa49.

2. A pharmaceutical composition for treating or preventing a group q streptococcal infection comprising an antibody or antiserum according to claim 1 and a pharmaceutically acceptable carrier or excipient.

3. A diagnostic kit for determining the presence of Cpa1 or Cpa49 proteins comprising antibodies reactive with either Cpa1 or Cpa49 and means to introduce the antibodies to a sample.

4. A method of inducing an immunological response comprising administering to a patient a composition comprising an isolated protein selected from the group consisting of Cpa1, Cpa49 and active fragments thereof.

5. A method of treating or preventing a group A streptococcal infection in a patient comprising administering to the patient antibodies to a protein selected from the group consisting of Cpa1, Cpa49 and active fragments thereof in an amount sufficient to inhibit binding of Group A streptococci to collagen.

* * * * *